(12) United States Patent
Hager

(10) Patent No.: US 8,330,957 B2
(45) Date of Patent: Dec. 11, 2012

(54) DEVICE AND METHOD FOR QUANTIFICATION OF GASES IN PLUMES BY REMOTE SENSING

(75) Inventor: J. Stewart Hager, Knoxville, TN (US)

(73) Assignee: Hager Enviromental and Atmospheric Technologies, LLC, Knoxville, TN (US)

( * ) Notice: Subject to any disclaimer, the term of this patent is extended or adjusted under 35 U.S.C. 154(b) by 335 days.

(21) Appl. No.: 12/883,621

(22) Filed: Sep. 16, 2010

(65) Prior Publication Data

US 2011/0038507 A1    Feb. 17, 2011

Related U.S. Application Data

(63) Continuation-in-part of application No. 12/493,364, filed on Jun. 29, 2009, now Pat. No. 8,284,744.

(51) Int. Cl.
*G01N 21/00* (2006.01)

(52) U.S. Cl. .......................... 356/438; 356/432; 356/437

(58) Field of Classification Search .................. 356/446, 356/342, 432, 437, 438
See application file for complete search history.

(56) References Cited

U.S. PATENT DOCUMENTS

| | | |
|---|---|---|
| 4,489,239 A | 12/1984 | Grant et al. |
| 4,924,095 A | 5/1990 | Swanson, Jr. |
| 5,319,199 A | 6/1994 | Stedman et al. |
| 5,489,777 A | 2/1996 | Stedman et al. |
| 5,498,872 A | 3/1996 | Stedman et al. |
| 5,845,639 A | 12/1998 | Hochman et al. |
| 6,064,488 A | 5/2000 | Brand et al. |
| 6,455,851 B1 | 9/2002 | Lord et al. |
| 6,542,831 B1 | 4/2003 | Moosmuller et al. |
| 7,164,132 B2 | 1/2007 | Didomenico et al. |
| 7,183,945 B2 * | 2/2007 | DiDomenico et al. ........ 340/937 |
| 7,375,814 B2 | 5/2008 | Reichardt et al. |
| 2002/0092988 A1 | 7/2002 | Didomenico et al. |
| 2004/0104345 A1 | 6/2004 | Kansakoski et al. |
| 2006/0173355 A1 | 8/2006 | Alfano et al. |
| 2006/0188869 A1 | 8/2006 | Zeskind et al. |
| 2007/0164220 A1 | 7/2007 | Luk |
| 2009/0238438 A1 | 9/2009 | Wardlaw et al. |

FOREIGN PATENT DOCUMENTS

WO    2010026579 A2    3/2010

* cited by examiner

*Primary Examiner* — Roy M Punnoose
(74) *Attorney, Agent, or Firm* — Morris Manning & Martin, LLP; Tim Tingkang Xia, Esq.

(57) ABSTRACT

In one aspect, the present invention relates to a device quantifying absolute amounts of ingredients of a plume. In one embodiment, the device comprises a source for emitting a beam of light and transmitting the emitted light through the plume to a surface on which the transmitted light is scattered, a detector for acquiring an image of the exhaust plume, the acquired image containing information of absorption of the scattered light scattered from the surface, and a processor for processing the acquired image to determine an absolute amount of at least one of components of the exhaust plume.

15 Claims, 16 Drawing Sheets

$A_1$  $A_2$  $A_3$ . . . $A_n$ . . . . . . . . . . . . $A_N$

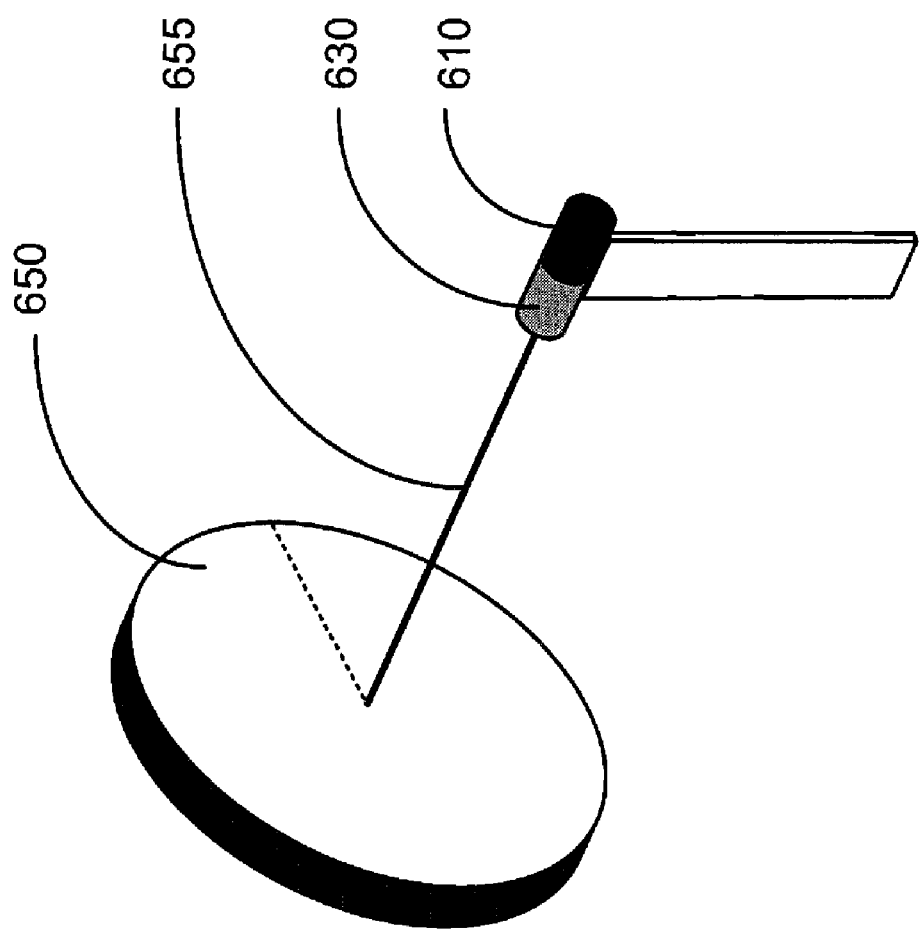

DEVICE AND METHOD FOR QUANTIFICATION OF GASES IN PLUMES BY REMOTE SENSING

CROSS-REFERENCE TO RELATED PATENT APPLICATION

This application is a continuation-in-part of U.S. patent application Ser. No. 12/493,634, filed Jun. 29, 2009, entitled "DEVICE FOR REMOTE SENSING OF VEHICLE EMISSION," by J. Stewart Hager, which is incorporated herein in their entireties by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

FIELD OF THE INVENTION

The present invention generally relates to remote detection of emission, and more particularly to an apparatus and method that utilize optical masses for quantifying absolute amounts of ingredients of a plume using remotely acquired infrared and ultraviolet images of the plume.

BACKGROUND OF THE INVENTION

It is known that vehicle emissions are a major contributor to air pollution. In order to identify vehicles that are releasing excessive polluting emissions, many countries mandate annual vehicle emission inspections. To this purpose various vehicle emission inspection systems have been developed. Generally, these systems can be very expensive, and their operation can require a vast amount of labor and skill. Additionally, emission inspection systems have traditionally been operated in testing stations where the emissions are measured when the test vehicle is idling or running under artificially loaded conditions. Although such measurements provide general baseline information regarding a vehicle's emissions and state of repair, it is not necessarily representative of "real world" driving conditions.

Recently, remote emission sensing systems have been developed for detecting emissions of vehicles as they are driving on the road. For example, U.S. Pat. Nos. 5,319,199 and 5,498,872 to Stedman et al. discloses a remote sensing system in which the light source 1110 and detector 1130 are oppositely located on both sides of the road 1101, respectively, as shown in FIG. 11(*a*). For such an arrangement, a beam of light 1115 generated from the source 1110 passes through an exhaust plume 1140 emitted from a vehicle 1105 driven on the road 1101, thereby carrying an absorption signal associated with components and concentrations of the exhaust plume 1140. The beam 1115 is collected by the detector 1130 for analyzing the components and concentrations of exhaust plume 1140. Alternatively, as shown in FIG. 11(*b*), the light source 1110 and detector 1130 are located on the same side of the road 1101. And two reflectors 1150 located on the opposite side of the road 1101 are used to reflect the beam 1115 generated from the source 1110 to the detector 1130 with two passes through the vehicle exhaust plume 1140, which increases the absorption signal. This system measures only part of the plume and has to ratio the $CO_2$ measurements to all other pollutants to get relative values. It does not measure the amount left behind or absolute values.

However, for such remote emission sensing systems, the source, detector and reflectors are set up on both sides of the road, and much care needs to be taken during their installation and maintenance. Additionally, such a system is difficult to operate with more than one lane of traffic particularly when more than one vehicle passes through the detector simultaneously. In other words, if multiple vehicles are present at the sensing location, each vehicle's exhaust plume may contribute equally to the emission measurement. Thus, on a single lane road, such as entrance and exit ramps, the existing remote sensing systems are not able to detect more than one exhaust plume at a time.

Furthermore, with current remote sensing systems the precision of the measurement can also depend on the position of the beam of light going across the road since the location of the vehicle's one or more exhaust pipes can vary from vehicle to vehicle. The precision of the emissions measured will vary depending on whether the beam is at the height of the tail pipe, or lower or higher where the exhaust has time to dilute before detection. With such an arrangement is also possible to miss the exhaust plume altogether.

Ultimately, the main drawback to current remote emission sensing is that since it only measures a portion of an exhaust plume it can only determine a plume's constituent gases and their relative concentrations. While such results can indicate if a vehicle is in need of repair, existing systems are not able to measure absolute amounts of emission components. Measuring absolute amounts of components is important since a surfeit can lead to severe air pollution. It is for this reason that many countries statutorily limit the amount of gas pollutants allowed in emissions. In fact, state and federal vehicle emissions standards and control requirements are stated in "grams per mile." With existing systems this value must be extrapolated from the ratios reported by identifying the vehicle make and model and making assumptions about whether the vehicle is running rich or lean, the load on the vehicle, etc.

Quantitative imaging of gas emissions techniques has been patented. For example, U.S. Pat. No. 5,319,199 describes an elaborate system which uses gas self-emission radiation and gas filled cells. Unfortunately, the complexity of this method is unnecessary and cost prohibitive.

Therefore, a heretofore unaddressed need exists in the art to address the aforementioned deficiencies and inadequacies.

SUMMARY OF THE INVENTION

The objectives of the present invention are to measure absolute values of ingredients in an exhaust plume using infrared and/or ultraviolet images of the plume. By measuring the percent absorption of individual pixels in the images and their projected area, one can calculate the total amount of a constituent in the plume.

In one aspect, the present invention relates to a device quantifying absolute amounts of ingredients of a plume. In one embodiment, the device comprises a source for emitting a beam of light and transmitting the emitted light through the plume to a surface on which the transmitted light is scattered and reflected; a detector for acquiring an image of the plume, where the acquired image contains information of absorption of the light scattered and reflected from the surface; and a processor for processing the acquired image to determine an absolute amount of at least one of components of the visible plume.

The processor is configured to perform the steps of choosing a plurality of pixels from the acquired image along a section crossing the plume, each pixel having a pixel area; characterizing an absorption rate of light of each chosen pixel from the acquired image; calculating the optical mass of each pixel from the characterized absorption rate of the pixel; multiplying the optical mass of a pixel and the corresponding projected pixel area to obtain the number of molecules in the pixel; and summing the number of molecules of each pixel to obtain the total number of molecules in the visible plume.

In one embodiment, Beer's Law determines the optical mass μ of each pixel:

$$\mu = -\ln(I/I_0)/\kappa(v),$$

where $(I/I_0)$ is associated with the absorption rate, and $\kappa(v)$ is a monochromatic absorption coefficient.

Light detection and ranging (LIDAR) is a broad term that includes scattering, fluorescence, absorption, and differential absorption and scattering (DAS). Differential Absorption LIDAR (DIAL) is a commonly used technique to measure column abundances of gases in the atmosphere. The method uses two different wavelengths of light to make the measurement. One wavelength is centered on to an absorption feature of the target gas and a second wavelength closes to the first wavelength but away from the absorption feature. The two different absorptions are compared and the column abundance is calculated using the DIAL equation.

Detecting vehicle exhaust serendipitously allows one to use the DIAL equation with just one wavelength. The second wavelength can be substituted with the measurement using the first wavelength just before the vehicle arrives.

In one embodiment, the source comprises a black-body light source such as a halogen light bulb or a "glowbar" gas igniter. Accordingly, the device further has a collimating or spreading optics for the emitted light and transmitting the light through the plume to the surface. The collimating or spreading optics comprise a first concave mirror and a second concave mirror positioned in relation to the source such that the first concave mirror receives the beam of light emitted from the source and reflects the received light to the second concave mirror, the second concave mirror, in turn, collimates or spreads the reflected light and transmits the light through the plume to the surface of the lane. The first concave mirror and the second concave mirror define a focus therebetween, and a chopper is placed on the focus.

In another embodiment, the source comprises one or more narrowband source like LED devices or filtered broadband sources. In yet another embodiment, the source comprises one or more coherent sources or lasers.

In yet another embodiment, the source is the natural sunlight. As long as the entire plume along with its "shadow" is imaged, all molecules are double-passed by the light. One can then retrieve the total amount of targeted molecules in the plume using double pass retrieval methods.

Additionally, the source can be modulated which enables the measurement of light transmitted through hot exhaust since hot exhaust itself radiates infrared light relative to the colder background. When the active source is blocked by a chopper or turned off, a measurement of the emission of the exhaust is made. The emission of the exhaust plume can then be subtracted from the measurement when the active source is unblocked or turned on to obtain only the transmission of the hot exhaust. Other well known modulation/demodulation techniques can be used as well.

Alternatively, a modulated source can be used such as LEDs and lasers to achieve the same effect.

The reflective surface can be the road itself or some form of retroreflective material.

In one embodiment, the detector comprises at least one of an infrared camera and/or an ultraviolet camera with narrow bandpass filters, wherein the filters incorporate the absorption bands of specific gases. In another embodiment, the detector comprises a detector array capable of capturing images of the plume and the surface. In yet another embodiment, the detector comprises a plurality of photosensors, each photosensor generating an electrical signal responsive of the received light, wherein the electrical signal is indicative of the absorption of the received light by the plume. In one embodiment, the detector comprises a spectrometer, a focal plane array, a linear array, a single element or any combination of them.

In a further embodiment, the detector comprises a detector array capable of capturing images of the plume and the surface.

In one embodiment, the source comprises a halogen light source. Accordingly, the device further has a collimating optics for collimating the emitted light and transmitting the collimated light through the plume to the surface. The collimating optics comprises a first concave mirror and a second concave mirror positioned in relation to the source such that the first concave mirror receives the beam of light emitted from the source and reflects the received light to the second concave mirror, the second concave mirror, in turn, collimates the reflected light and transmits the collimated light through the plume to the surface of the lane. The first concave mirror and the second concave mirror define a focus therebetween, and a chopper is placed on the focus.

In another embodiment, the source comprises a laser or modulated laser.

In another aspect, the present invention relates to a method for quantifying absolute amounts of ingredients of a plume. In one embodiment, the method includes the steps of directing a beam of light through the plume to a surface on which the beam of light is scattered; acquiring an image of the plume, the acquired image containing information of absorption of the scattered light scattered from the surface; and processing the acquired image to determine an absolute amount of at least one of components of the plume.

The processing step comprises the steps of choosing a plurality of pixels from the acquired image along a section crossing the plume, each pixel having a pixel area; characterizing an absorption rate of light of each chosen pixel from the acquired image; calculating optical mass of each pixel from the characterized absorption rate of the pixel; multiplying the optical mass of a pixel and the corresponding pixel area to obtain the number of molecules in the pixel; and summing the number of molecules of each pixel to obtain the total number of molecules in the plume.

In one embodiment, the image of the plume is acquired by an infrared camera and/or an ultraviolet camera with narrow bandpass filters, wherein the filters incorporate the absorption bands of specific gases. In another embodiment, the image of the plume is acquired by a plurality of photosensors.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, wherein:

FIG. 7 shows schematically a collecting optics utilized in the remote sensing device according to another embodiment of the present invention;

DETAILED DESCRIPTION OF THE INVENTION

Figure 1A:
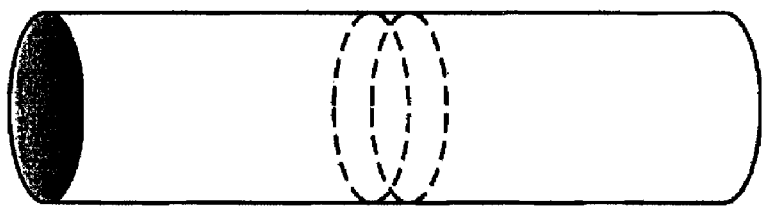
FIGS. 1(a)-1(e) illustrate a method of using the optical mass for quantifying absolute amounts of ingredients of a plume according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "LIDAR" is an acronym or abbreviation of "light detection and ranging", and is an optical remote sensing technology that measures properties of scattered light to find range and/or other information of a distant target. Differential Absorption LIDAR (DIAL) is a commonly used technique to measure column abundances of gases in the atmosphere.

As used herein, the term "optical mass" is a measure of the total number of absorbing molecules per unit area occurring along the direction of propagation of the radiation in a gas sample.

As used herein, the terms "comprising," "including," "having," "containing," "involving," and the like are to be understood to be open-ended, i.e., to mean including but not limited to.

The description will be made as to the embodiments of the present invention in conjunction with the accompanying drawings in FIGS. 1-10. In accordance with the purposes of this invention, as embodied and broadly described herein, this invention, in one aspect, relates to an apparatus that utilizes the LIDAR technology to detect emissions of a vehicle as well as the amount of at least one of the pollutants emitted from the vehicle. The invented device is a portable or permanent roadside system for detection of exhaust emissions of a vehicle having internal combustion engines and driven on a lane of a road. While the conventional emission detection devices use mirrors or retro reflectors to return a beam of light emitted from a source and transmitted through an exhaust plume of the vehicle to a detector, the invented device uses the LIDAR technology. The beam of light emitted from a source is directed downwards, passing through the exhaust plume, toward the surface of a traffic lane of a road on which the vehicle is driven. The transmitted light is then scattered at the surface of the traffic lane. The invented device collects the scattered light from the surface of the traffic lane for the detector to receive. Further, a detector array can be utilized to acquire images of the exhaust plume and the surface of the road for determining the intensity of the received light absorbed by the exhaust plume.

Specifically, the device utilizes the optical masses for quantifying absolute amounts of ingredients of a plume using remotely acquired infrared and ultraviolet images of the plume. The optical mass is a measure of the total number of absorbing molecules per unit area occurring along the direction of propagation of the radiation in a gas sample such as a plume or vapor, i.e., $\mu = \rho_{molecules} \cdot l = N_{molecules}/\hat{A}$, where $\rho_{molecules}$ is the number density of molecules, l is the length of the cylinder, $N_{molecules}$ is the number of molecules in a unit area and $\hat{A}$ is the unit area. Accordingly, the amount of a gas in a plume is equal to the optical mass multiplied by the projected area of the plume, that is, $N_{cell} = \mu^* A_{total}$, the optical mass is multiplied by the area of the gas cell perpendicular to the direction of propagation of the radiation to acquire the total number of molecules of the specific gas in the cell. The total number of molecules can then be divided by Avogadro's number to get moles. Then the total mass of a specific gas in the cell is just the molar mass or atomic weight of the molecule multiplied by the number of moles. This technique is utilized with in situ devices to measure the concentrations of pollutants coming from an exhaust pipe. The in situ device draws the exhaust into a gas cell through a hose attached to the tailpipe, for the absorption to be measured.

Figure 1B:
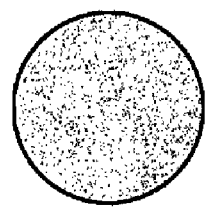
Figure 1C:
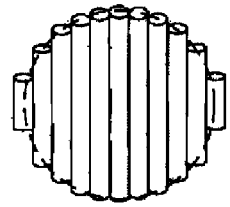
Figure 1D:
Figure 1E:

FIGS. 1(a)-1(e) illustrate the method/principle of using the optical mass for quantifying absolute amounts of ingredients of a plume according to one embodiment of the present invention. Usually, the plume is observed from the top or side for remote sensing purposes. For the illustration of the present invention, the gas cell is looked at from the top and assumed as a cylindrical plume, as shown in FIG. 1(a). As shown in FIGS. 1(b) and 1(c), a small disc is cut and divided into smaller individual gas cells. Now the light is propagating perpendicular to the length of the cell. As the light propagates through the top of the disc it will have different path lengths. Looking through the top of the disc one will see different absorptions due to the different path lengths, as shown in FIG. 1(d). Each small cell will approximately have a constant absorption over the width of the cell, shown in FIG. 1(e). Then, the area of the ends of the smaller absorption cells is calculated and multiplied by the optical mass of each cell to get the number of molecules in each cell. The N molecules are added in each small cell to get the total number of molecules in the disc, i.e., $$N_{disc} = \sum_{i=1}^{N} \mu_i \cdot A_i.$$

The total number of molecules or mass of a specific species in the disc is known. If the concentration of the chosen gas is uniformly mixed in the cell and the disc width is unit length, then the total number of molecules is $N_{molecules} = N_{disc}*l$. This number is the same as the first calculated number along the length of the cell.

As a vehicle travels down a road, it leaves a plume of exhaust behind. If one can take a section of the exhaust plume and count the molecules in the section, one could estimate the amounts of pollutants the vehicle is leaving behind. According to the present invention, images of the plume are acquired using infrared and/or ultraviolet cameras with narrow bandpass filters. These filters incorporate the absorption bands of specific gases. The images would show a plume coming out of the exhaust pipe for a specific gas.

Each pixel in the images can be considered as detecting an individual light beam with a gas cell in the path. The size and shape of these beams can be calculated using simple geometric techniques. The image of the road without a vehicle is used to measure the baseline intensity and then the absorption of a section of pixels across the plume is calculated, and thus, the change in optical mass of each pixel $\mu_i$ is calculated. Then the each change in optical mass $\mu_i$ is multiplied by the area $A_i$ perpendicular to direction of propagation to get the number of molecules per pixel and those quantities are added together to get the total number of molecules of a specific gas in the section of the plume. Then, the number of molecules is multiplied by the atomic weight to get the mass of the targeted molecule in the section of the plume i.e., $N_{section}*AMU$ (g/molecule)$=N_{grams}$. The width of the section can be utilized to calculate grams per distance the vehicle is spewing out. Likewise with a fixed source, the speed of the flow can be utilized to calculate grams per time the source is spewing out.

Figure 1F:
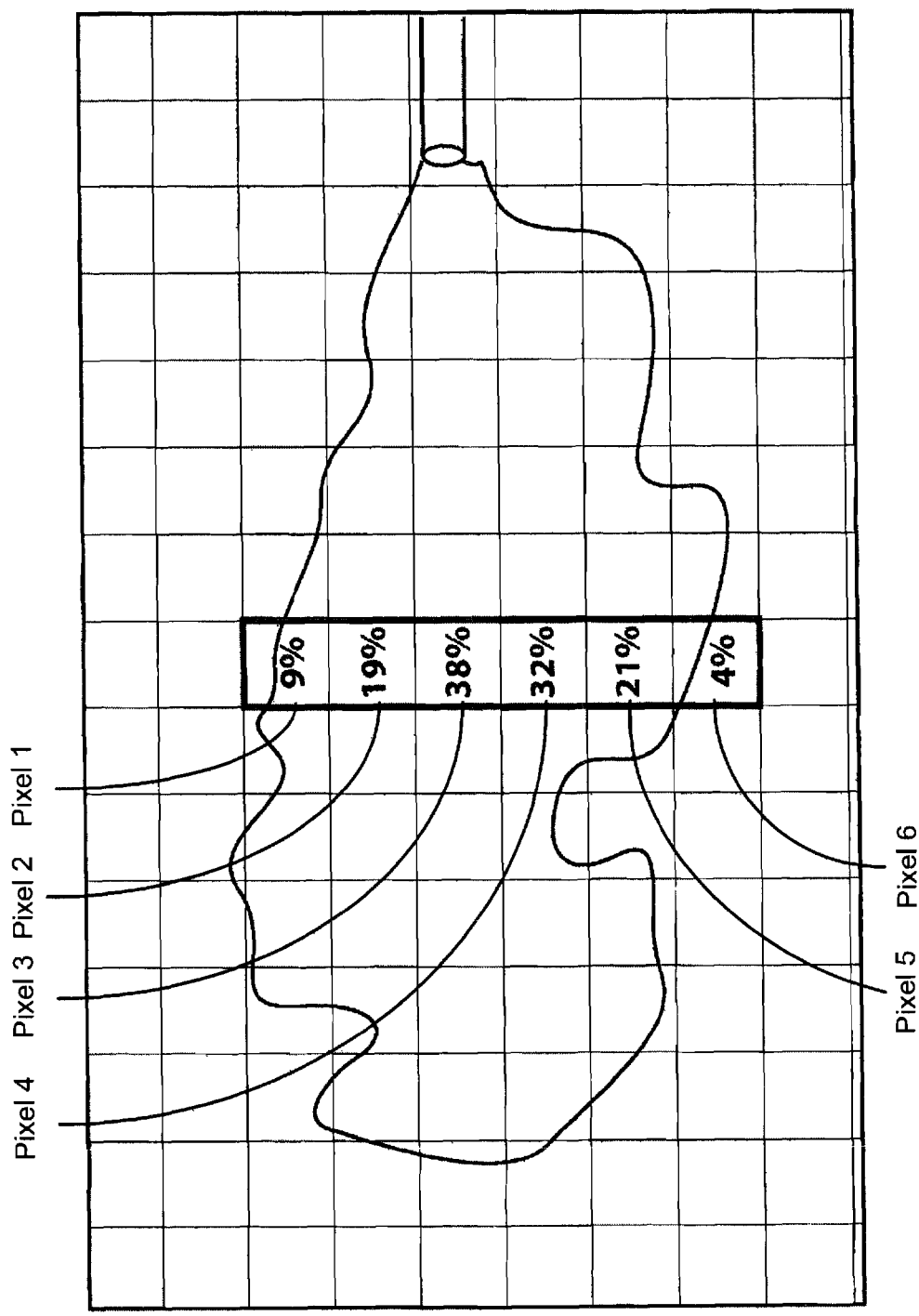
FIG. 1(f) shows an example for calculating absolute amounts of a plume from its image at chosen pixels, where each box represents a pixel in an image of the plume, and the percentages are the absorption in each pixel due to the target gas.

According to the present invention, by examining a picture/image of an exhaust plume, the amount of a substance in the plume can be determined. FIG. 1(f) shows an example of the calculations needed to retrieve absolute amounts. Each box in FIG. 1(f) represents a pixel in an image of the exhaust plume. The distance away from the plume is considered large enough so that each pixel has approximately the same area from the top to the bottom of the plume. The percentages are the absorption in each pixel due to the target gas. These percentages can be found two ways. One way is by comparing the image of the road just before the car arrives to the image of the exhaust plume. The ratios of the reflected light from a source next to the camera will give the percentages. These percentages can also be found by DIAL (Differential Absorption LIDAR) methods using two different wavelengths of light, one at resonance and the other off resonance. Using Beer's law, the optical mass of each pixel is obtained. Then the area of that pixel is used to calculate the total number of molecules in that pixel.

For example, the band strength of a chosen band of Carbon Dioxide is:

$\kappa(Band)_{CO2} = 0.9$ cm$^{-2}$atm$^{-1}$ at *STP*.

The units are converted into cm$^{-1}$ [cm$^2$ mol$^{-1}$]:

$\kappa(Band)_{CO2} = (0.9*2.2414*10^4)$cm$^{-1}$ [cm$^2$mol$^{-1}$] = 20173.0 cm$^{-1}$ [cm$^2$mol$^{-1}$].

Using the equivalent width method and for simplicity assuming the weak line limit, we know the equivalent width is equal to $\kappa(Band) \cdot \mu$. The equivalent width is:

$$W = \int_{-\infty}^{\infty} (1 - \exp(-\kappa(Band) \cdot \mu)) dv$$

or the total area of the absorption band.
The area of each pixel is about 20 cm*20 cm=400.0 cm$^2$:

$\mu = -\ln(I/I_0)/\kappa(Band)$, and Number of Moles$=\mu^*$Area

| Chosen Pixel No. | $\mu = -\ln(I/I_0)/\kappa(Band)$ (mol cm$^{-2}$) | No. of Moles = $\mu$ *Area (mol) |
|---|---|---|
| 1 | 4.6751 × 10$^{-6}$ | 1.8700 × 10$^{-3}$ |
| 2 | 1.0446 × 10$^{-5}$ | 4.1784 × 10$^{-3}$ |
| 3 | 2.3697 × 10$^{-5}$ | 9.4788 × 10$^{-3}$ |
| 4 | 1.9118 × 10$^{-5}$ | 7.6472 × 10$^{-3}$ |
| 5 | 1.1685 × 10$^{-5}$ | 4.6740 × 10$^{-3}$ |

-continued

| Chosen Pixel No. | $\mu = -\ln(I/I_0)/\kappa(\text{Band})$ (mol cm$^{-2}$) | No. of Moles = $\mu$ *Area (mol) |
|---|---|---|
| 6 | $2.0236 \times 10^{-6}$ | $8.0944 \times 10^{-4}$ |
| | Total Mole Number | $2.8658 \times 10^{-2}$ |

Therefore, the absolute amount of $CO_2$ in the chosen pixels is $2.8658 \times 10^{-2}$ mol or $2.8658 \times 10^{-2}$ mol*44.01 (g/mol) =1.2612 g.

EPA, though, uses units such as (g/mi). To convert to (g/mi), (cm/mi) is needed, which is $1.6093 \times 10^5$ (cm/mi). The vehicle leaves behind 1.2612 g of $CO_2$ every 20 cm, it is about $1.0148 \times 10^4$ g of $CO_2$ per mile.

Figure 2A:
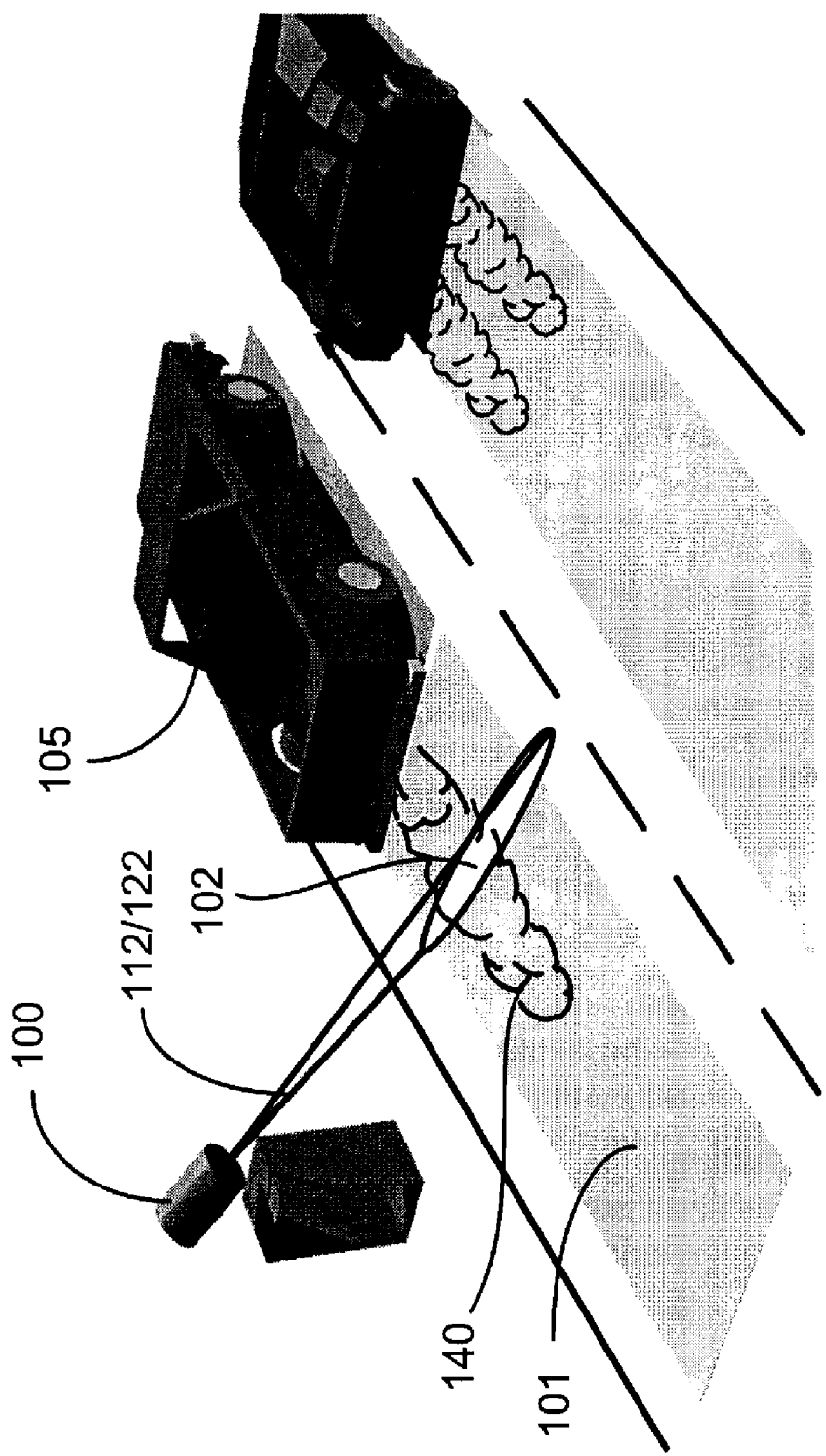
FIG. 2(a) shows schematically a device for remote sensing of vehicle emission according to one embodiment of the present invention.
Figure 2B:
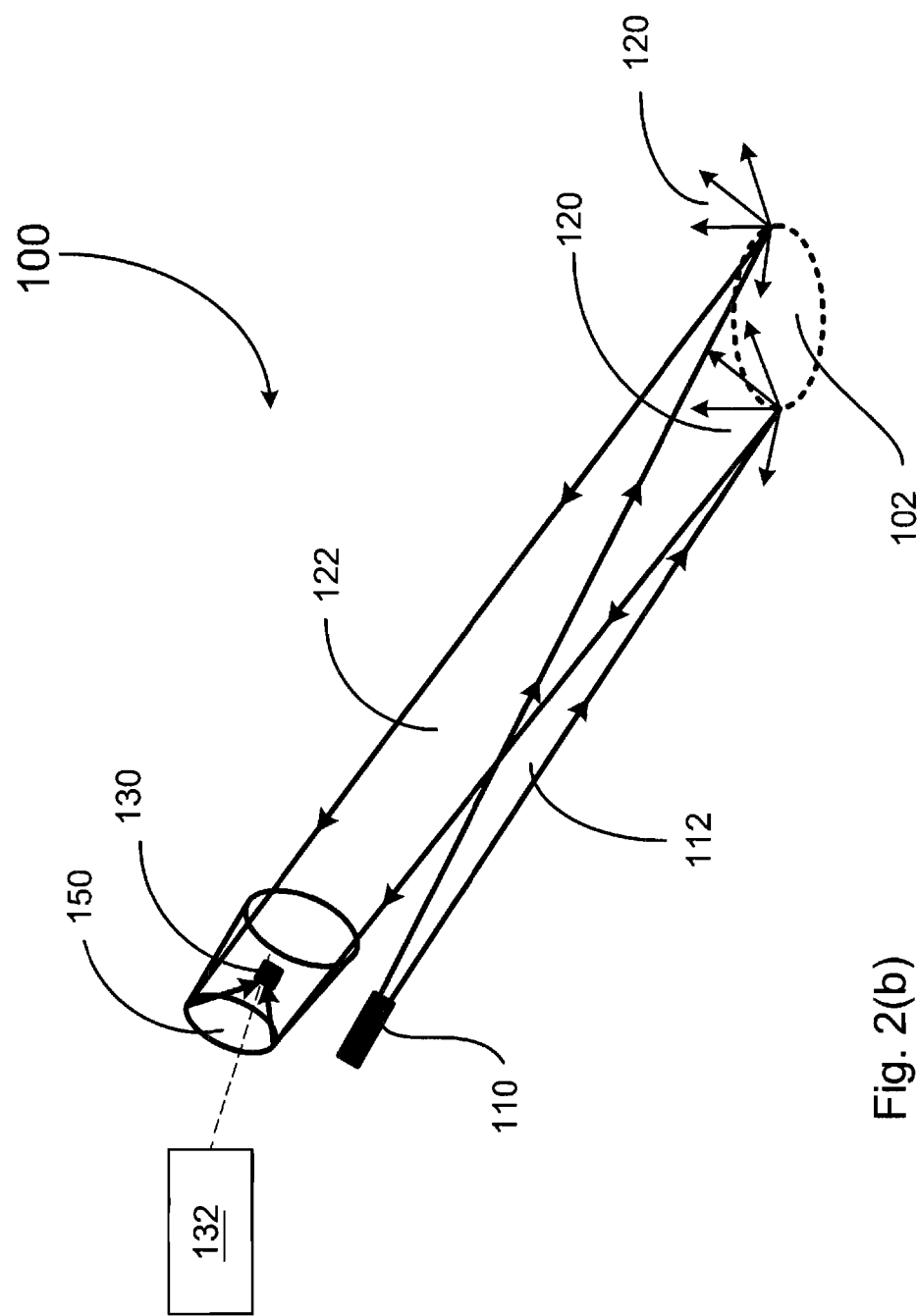
FIG. 2(b) shows schematically an optical diagram of the remote sensing device according to one embodiment of the present invention.

Referring to FIGS. 2(a) and 2(b), and particularly to FIG. 2(b), a device 100 for remote sensing of vehicle emission is shown schematically according to one embodiment of the present invention. The device 100 includes a source 110, a detector 130 and an optical collecting optics 150. The source 110 and the detector 130 define an optical path along which a beam of light travels from the source 110 to the detector 130, and the collecting optics 150 is positioned in the optical path. Further, the source 110, the detector 130 and the collecting means 150 are located in the same side of the road.

While in operation, a beam of light 112 emitted from the source 110 is scattered, in a $2\pi$ steradian hemisphere, at a surface 102 of the lane 101 of the road on which a vehicle 105 is driven. A received light 122, portion of the scattered light 120 along the optical path, is collected by the concave mirror (the collecting optics) 150. The collecting optics 150, in turn, delivers the received light 122 of the scattered light 120 to the detector 130 that is located at the focus of the collecting optics 150.

According to one embodiment of the present invention, the detector 130 comprises a camera with a focal plane array. The emitting light source comprises a halogen bulb and/or a glow-bar such as natural gas igniter. In another embodiment, the detector 130 comprises a plurality of photosensors, thereby corresponding to a plurality of pixels. A pixel can be corresponding to one or more photosensors. To clarify the embodiments described as below, the case that one pixel corresponds to one photosensor is established therein the embodiments are based on. Nevertheless, illustrations and description are not intended to be exhaustive or be limited to the scope of the invention disclosed. Alternative pixel relatively to a plurality of photosensors is possible as well.

The camera 130 for receiving the received light 122 shall be set next to the source 110 and thus used to picture the state of the lane 101 as an imaging camera for obtaining the optical intensity of the received light 122. Since the detector 130 can be used to transfer the optical signals into electrical signals, the device 100 furthermore comprises a processor 132 in communication to the detector 130 so as to process the electrical signals.

Figure 3A:
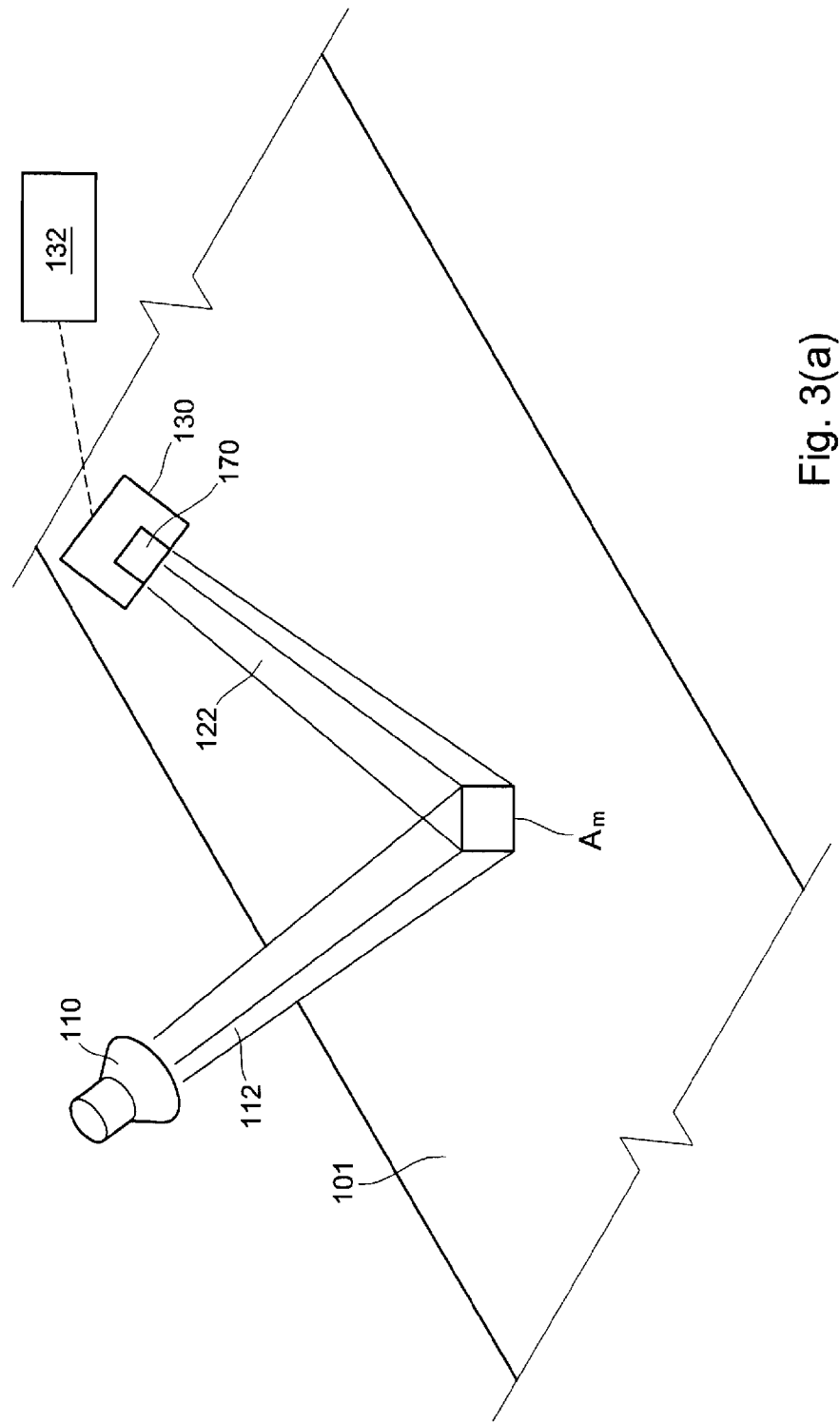
FIG. 3(a) shows schematically the device for imaging a first state of the lane when no detected vehicle arrives according to one embodiment of the present invention.

For instance, referring to FIG. 3(a), when at least one part of the beam of light 112 can be incident to one pixel 170 the detector 130 is characterized by, the detector 130 in the first place can be used to picture the state of the lane 101 and to detect a first optical intensity of the received light 122 while no detected vehicle is passing through.

Figure 3B:
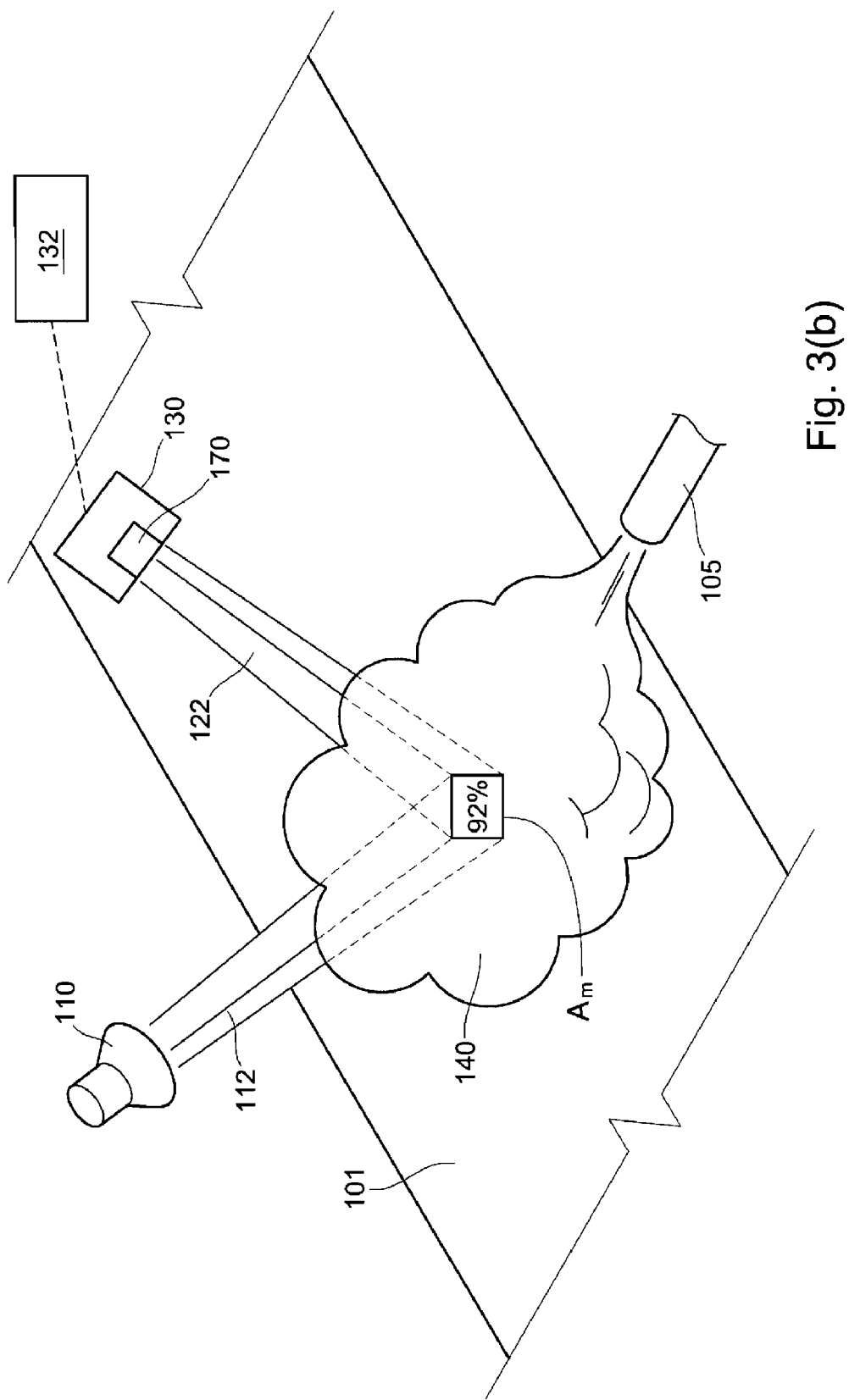
FIG. 3(b) shows schematically the device for imaging a second state of the lane when the detected vehicle arrives leaving behind the exhaust plume according to one embodiment of the present invention.

Moreover referring to FIG. 3(b), after the vehicle 105 passes through the surface 102 of the lane 101 and leaves behind the exhaust plume 140, the detector 130 further images the state of the lane 101 and detects a second optical intensity of the received light 122 transmitted through the exhaust plume 140. Under such circumstances, the distance away from the exhaust plume 140 is considered large enough so that the pixel 170 has approximately the same area from the top to the bottom of the exhaust plume 140.

By comparing the former to the latter image, the processor 132 in communication with the detector 130 can not only process the electrical signals transferred from the optical signals of the received light 122 therein to provide one or more spectra of the received light 122 but also accordingly give the difference between the first optical intensity and the second optical intensity of the received light 122. Hence, as shown in FIG. 3(b), an attenuated ratio of the second optical intensity to the first optical intensity of the spectrum is obtained.

Figure 3C:
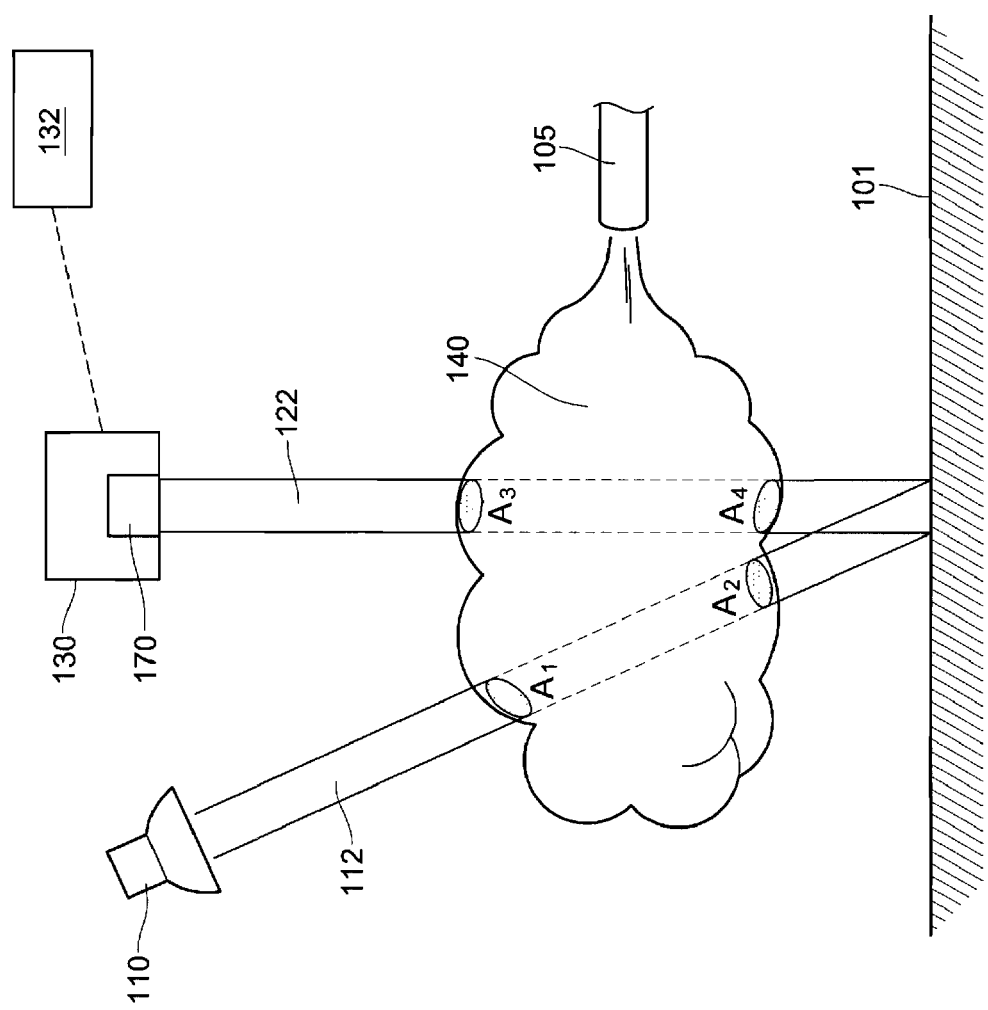
FIG. 3(c) shows schematically the transmitted path of the beam of light.

Besides, following by the detector 130, the processor 132 processing the electrical signals transferred from the optical signals of the received light 122 therein measures a detected area $A_m$ which is a cross sectional area of the exhaust plume 140 by which the received light 122 is absorbed. Referring to FIG. 3(c), when the beam of light 112 is emitted from the vehicle 105, scattered, and collected by the detector 130, on its transmitted path exposed to the exhaust plume 140, a first area $A_1$, a second area $A_2$, a third area $A_3$, and a fourth area $A_4$ are formed. Hereby given the optimization, the first area $A_1$, the second area $A_2$, the third area $A_3$, and the fourth area $A_4$ are about equal to one another. The detected area $A_m$, any of the four areas $A_1$-$A_4$, is measured.

On the account of Beer's law:

$$\mu = -\ln(I/I_0)/\kappa(v).$$

The processor 132 can be used to obtain an optical mass independent of the concentration or the path length of the exhaust plume 140, wherein $\mu$ is the optical mass, $(I/I_0)$ is the attenuated ratio and $\kappa(v)$ is a monochromatic absorption cross-section corresponding to the spectrum. Multiplying the optical mass by the detected area $A_m$, the processor 132 can be utilized to give an amount of the determined component of the exhaust plume 140.

In another embodiment of the present invention, the detector 130 may furthermore include a plurality of pixels 170 corresponding to a plurality of photosensors 160, wherein one pixel 170 corresponds to one photosensor 160. The photosensor 160 can be used to transfer the optical signals the detector 130 detects into electrical signals thereby the processor 132 comprised by the device 100 in communication to the detector 130 can accordingly process with.

In operation, the detector 130 comprising a plurality of pixels 170 is located next to the source 110 so as to retrieve the state of the lane 101 as an imaging camera. When the vehicle 105 being detected arrives in the surface 102 of the lane 101, the exhaust plume 140 emitted from the vehicle 105 can also be pictured by the detector 130. Under such circumstances, the distance away from the exhaust plume 140 is considered large enough so that each pixel has approximately the same area from the top to the bottom of the exhaust plume 140.

The detector 130 is initially operated to acquire images of the surface 102 of the lane 101 when the vehicle 105 being detected has not arrived and therein the exhaust plume 140 is not formed yet so as to obtain the first intensity of the received light 122. After the vehicle 105 arrives and spews out the exhaust plume 140 which the received light 122 is transmitted through, the detector 130 again is utilized to picture the exhaust plume 140 so as to obtain the second intensity of the received light 122.

Figure 3D:
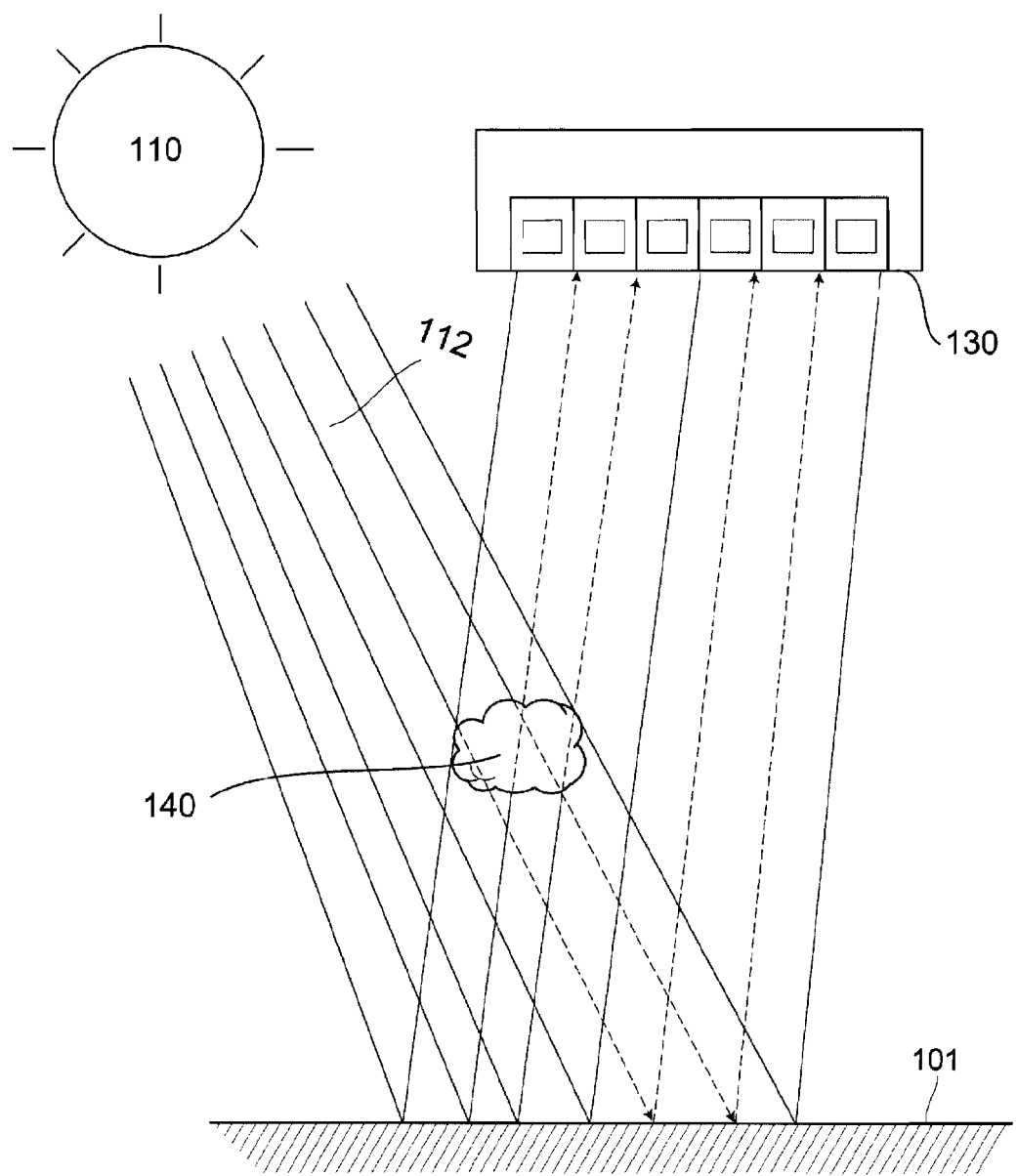
FIG. 3(d) shows schematically the device, illustrating that the light source and the detector do not have to be in the same optical axis in order to double-pass the whole section of the plume.

Alternately, in FIG. 3(d) the source 110 can be natural sunlight. As long as the entire plume 140 along with its' "shadow" is imaged, all molecules are double-passed by the light. One can then retrieve the total amount of targeted molecules in the plume 140 using double-pass retrieval methods.

Figure 4:
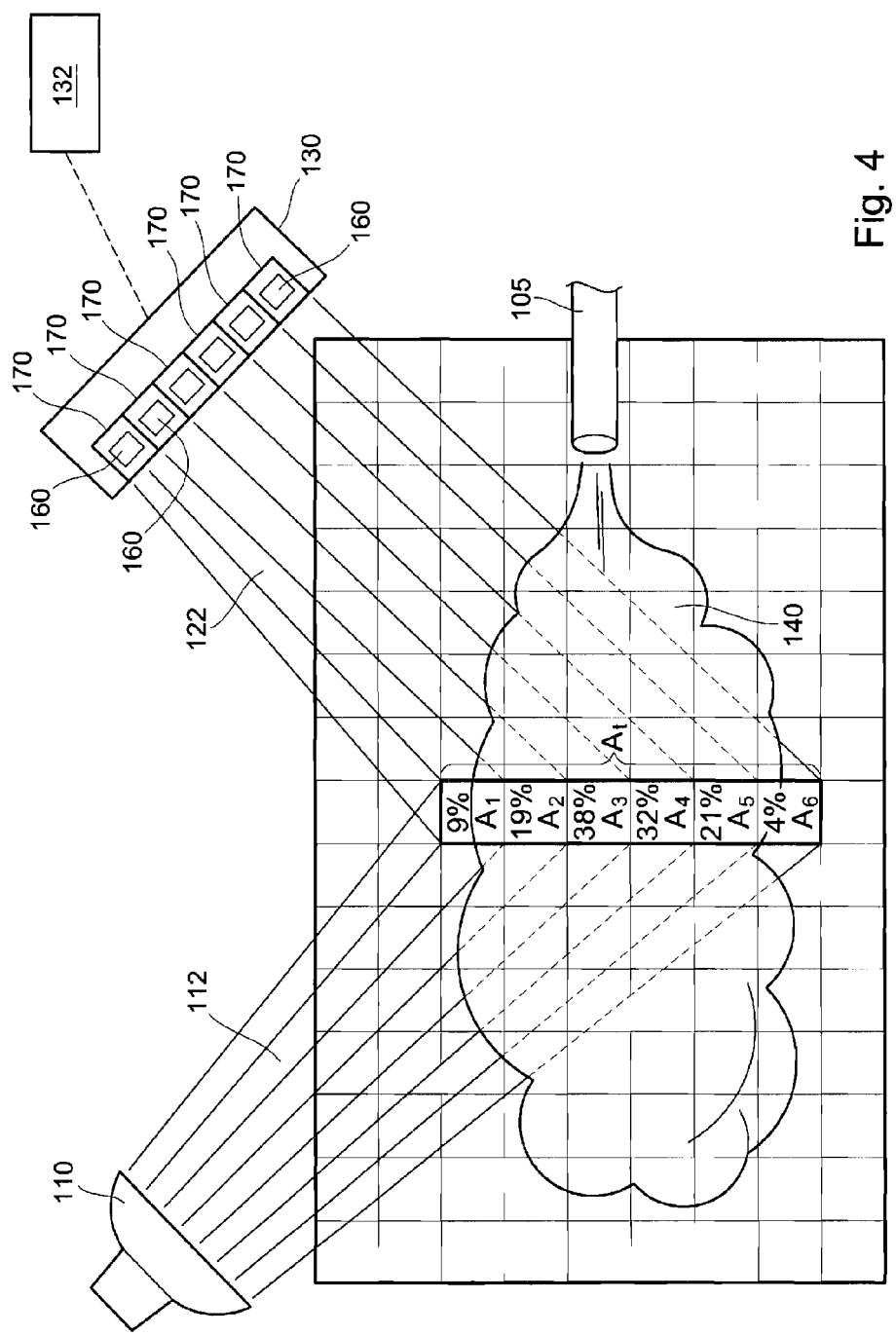
FIG. 4 shows schematically a device for imaging the state of the lane according to another embodiment of the present invention.

Practically, as shown in FIG. 4, each of the plurality of pixels 160 can be corresponding to a portion of the received light 122 and a portion of the total area $A_r$. Thus, involving with the detector 130, the processor 132 accordingly measures the pixel area $A_i$, wherein the number i is a positive integer. In one embodiment, the number i can be number of six, and $A_i$ comprises $A_1$, $A_2$, $A_3$, $A_4$, $A_5$, and $A_6$. The pixel area $A_i$ is the portion of the total area $A_r$. More accurately, the pixel area $A_i$ is a cross sectional area of the exhaust plume 140 by which the portion of the received light 122 is absorbed as shown as $A_1$, $A_2$, $A_3$, $A_4$, $A_5$, and $A_6$.

Since each photosensor 170 can be used to generate an electrical signal responsive of the portion of the received light 122 in each pixel area $A_i$ and each electrical signal is indicative of each optical difference in each pixel area $A_i$, representing each absorption percentage of the portion of the received light 122 absorbed by the exhaust plume 140, the processor 132 can be used to compare the image of the surface 102 of the lane 101 just before the vehicle 105 arrives to the image of the exhaust plume 140.

More specifically, the processor 132 can be used to process the electrical signals transferred from the optical signals of the received light 122 to have the absorption percentage and accordingly to obtain a plurality of pixel ratios $(I'/I_0')$ as numbers shown in FIG. 4.

Each of the pixel ratios $(I'/I_0')$ is corresponding to each pixel area $A_i$, wherein the pixel ratio $(I'/I_0')$ is an attenuated ratio of the second optical intensity to the first optical intensity of the portion of the received light 122 in each pixel area $A_i$.

In practice, the detector 130 comprising the plurality of pixels is utilized along with narrow band-pass filters. These filters incorporate the absorption bands of specific gases with a predetermined bandwidth thereof.

Hence, the processor 132 in communication of the detector 130 can be carried out to process the electrical signals transferred from the optical signals of the received light 122 therein so as to determine one or more spectra of the received light 122 and further to retrieve a plurality of sub optical masses $\mu_i$. Each of the sub optical masses $\mu_i$ is corresponding to the pixel area $A_i$, and the pixel ratios $(I'/I_0')$ based on Beer's law:

$$\mu_i = -\ln(I'/I_0')/\kappa(v),$$

where $\mu_i$ is the sub optical mass, $(I'/I_0')$ is the pixel ratio is and $\kappa(v)$ is a monochromatic absorption coefficient corresponding to the spectrum of the portion of the received light 122. Thereby the amount of the determined component can be summed up in the numbers of the plurality of pixels 160 with each product of the sub optical mass $\mu_i$ and the pixel area $A_i$, as $$\sum_{i=1}^{N} \mu_i \times A_i$$

wherein the number N is a positive integer and according to one embodiment, the number N is six.

In another embodiment of the present invention, the detector 130 may furthermore comprise a detector array capable of capturing images of the exhaust plume 140 and the surface 102 of the road.

In one embodiment, the processor 132 may have a computer and/or spectrometer. The processor 132 can also demodulate the detected beam of light.

Alternatively, what is described above in the specification while the second intensity and the first intensity of the received light 122 respectively refers to the point of time after and before the received light 122 passes through the exhaust plume 140 is not limited. One can easily substitute the two point of time as a late occurring point of time and an early occurring point of time for the foregoing definition even though both the point of time happens after the exhaust plume 140 is formed and therein the received light 122 has passed through the exhaust plume 140. In such application, the device 100 can still be applied to retrieve an amount of at least one of components of the exhaust plume 140 changed within a time period.

Additionally, the focal plane of the concave mirror 150 can be used to position several different detectors that image different sections of the road. One can image a strip of the road surface by using a parallel array detector.

Another embodiment involves using measurements using two filters imaging bands which contain different cross-sections of the same gas and using the DIAL equation to retrieve absolute amounts.

Different light sources are utilized requiring different configurations and detector technologies. The light sources are pulsed or chopped in accord with lock-in amplifiers to increase sensitivity and to differentiate light sources.

Figure 5:
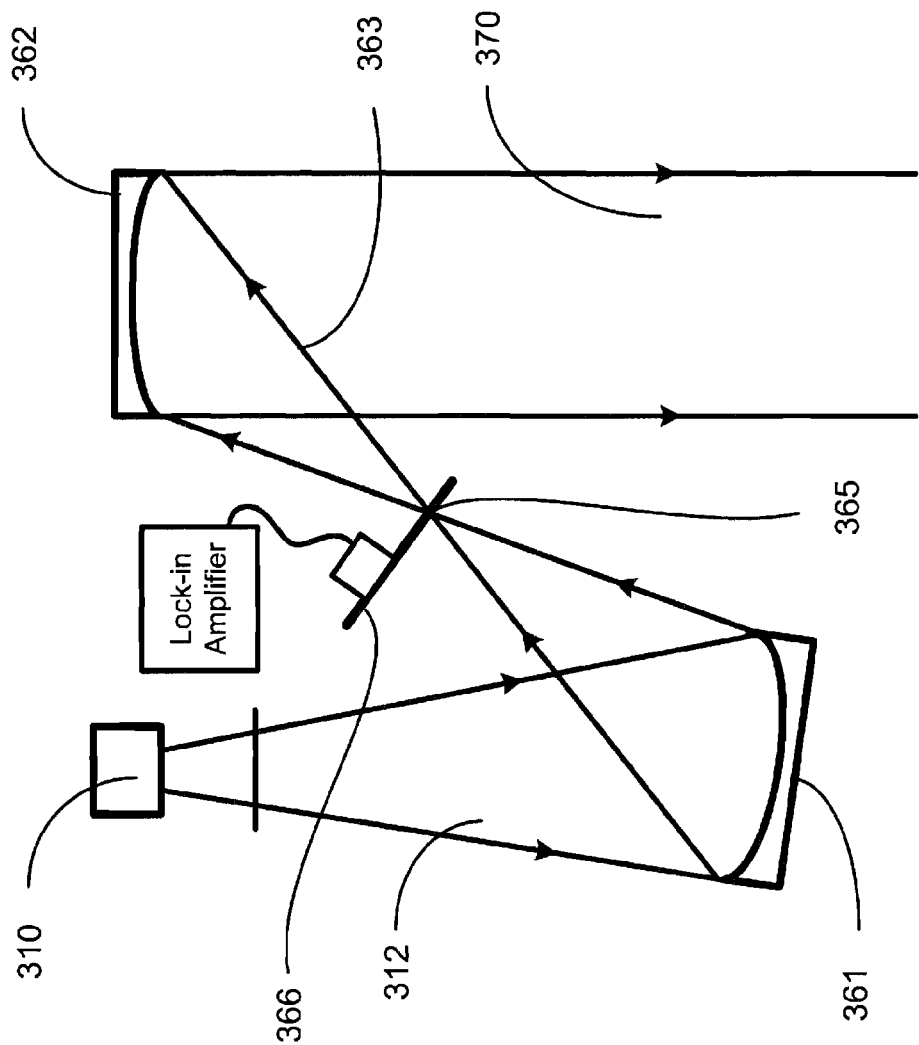
FIG. 5 shows schematically a collimating and speading optics utilized in the remote sensing device according to one embodiment of the present invention.

A Broadband Source—Halogen Light Bulb: In one embodiment, a halogen light bulb such as a car headlight is used as the source. For such a broadband source, a collimating optics can be utilized to collimate the beam of light emitted from the halogen light bulb and to transmit the collimated light through the exhaust plume to the surface of the lane. As shown in FIG. 5, the collimating optics includes a first concave mirror 361 and a second concave mirror 362 positioned in relation to the broadband source 310 such that the first concave mirror 361 receives the beam of light 312 emitted from the source 310 and reflects the received light 312 to the second concave mirror 362. The second concave mirror 362, in turn, collimates the reflected light 363 and transmits the collimated light 370 through the exhaust plume to the surface of the lane. The first concave mirror 361 and the second concave mirror 362 define a focus 365. At the focus 365, the reflected light 363 is chopped with a wheel or bell chopper 366. The chopper signal is fed in to a dual-phase lock-in amplifier. The lock-in amplifier then amplifies the signal without adding noise.

This broadband source radiates from ultraviolet to infrared light out to 5 μm. This covers strong fundamental absorption bands of CO and $CO_2$ as well as strong violet and ultraviolet bands of $NO_2$, NO and $SO_2$. Filters can be used to isolate specific bands of these molecules, along with water vapor, hydrocarbons, ammonia and others.

A modulated halogen light source is strong in intensity and can be scattered over the complete lane. The modulation can be synchronized with the detector in order to eliminate the need for phase locking. This allows one to subtract the background radiation due to the hot car exhaust to only get the absorption due to the exhaust. Mirrors can be used to collect the light anywhere it is shining. Depending on the focal length and distance, these mirrors can image specific illuminated positions on to a detector. This allows different paths or position to be used to target different tailpipe positions.

Narrow Band Sources: By filtering a broadband source or using LEDs, the need for filtering the detector can be eliminated.

Diode Lasers: The telecommunication industry through mass production has significantly lowered the cost of diode lasers. The telecommunication industry uses fiber optics and diode lasers to transmit large amounts of data, long distances. Because of the material of the fiber optics the average wavelength of these lasers is approximately 1.5 μm. There are infrared absorption bands of $CO_2$, CO, $H_2O$, $NH_2$ and others in this region. The laser diodes and InGaAs detectors are extremely inexpensive and extremely high quality because of the mass production and cost affectedness of sensitivity of the products. This allows for detection of these bands even though some are extremely weak.

Diode lasers can be used to remotely sense the temperature of exhaust, because of the Boltzmann factor and the extreme narrowness of a laser line. The thermal distribution of rotational levels is not simply given by the Boltzmann factor $e^{-E/kT}$. The number of molecules $N_J$ in the rotational level J of the lowest vibrational state at the temperature T is proportional to (G. Herzberg. *Spectra of Diatomic Molecules*, $2^{nd}$ ed. D. Van Nostrand Co. 1950):

$$N_J = (2J+1)e^{-BJ(J+1)hc/kT}$$

Figure 6:
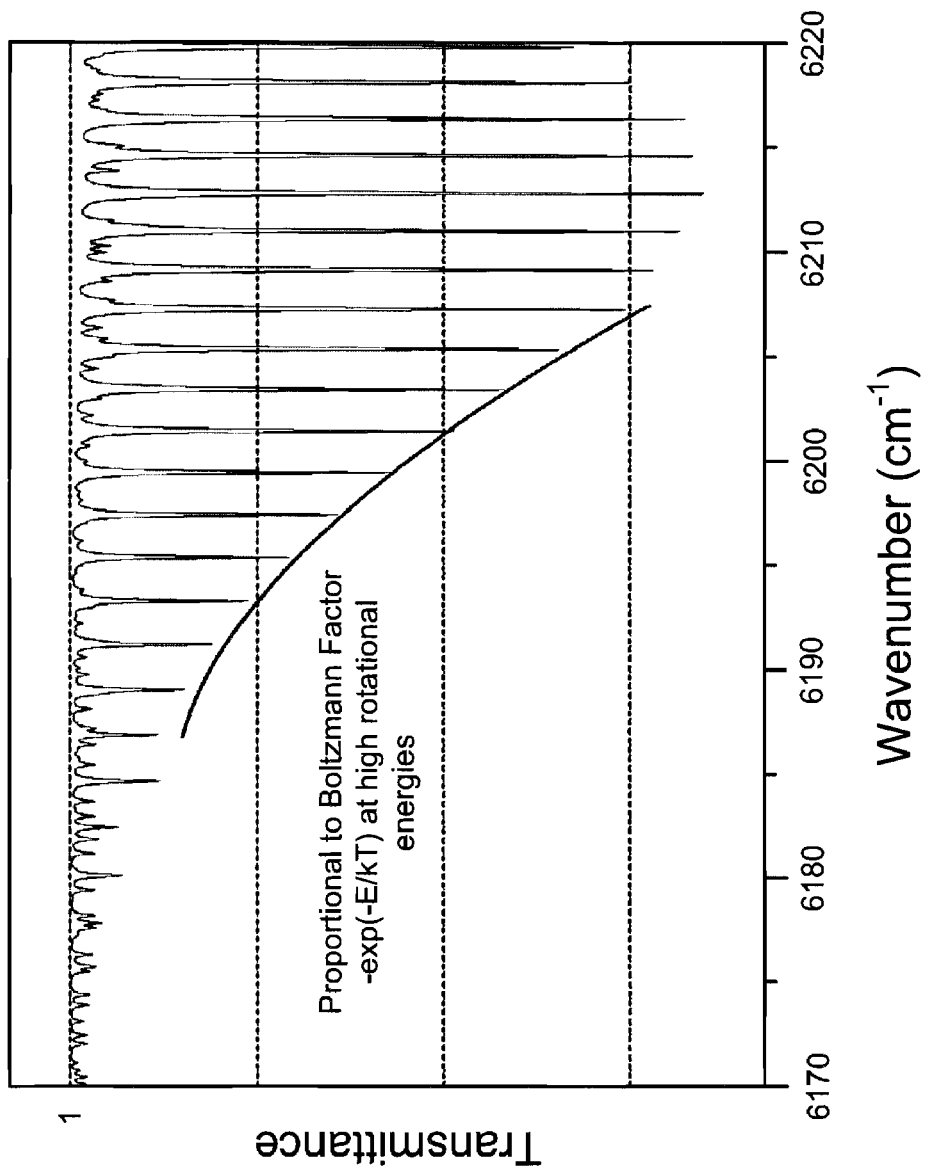
FIG. 6 shows the absorption lines at higher rotational energies follow the Boltzmann Factor.

This infers the higher the J value or rotational energy the more the exponential term dominates. One can then back out the temperature of the exhaust using this relationship. FIG. 6 shows the spectra of $CO_2$ in the 1.5 m region. The Boltzmann factor can be seen in the higher rotational energies. The absorption lines at higher rotational energies follow the Boltzmann Factor and therefore can be used to calculate the temperature of the exhaust.

Since the mixing ratio of molecules in the exhaust changes as a vehicle warms up, a cold car pollutes more than a hot one. One can detect the temperature along with the amount of gases in an exhaust plume using two or three different wavelength lasers. One can then adjust amount expectations due to the temperature of the engine and tailpipe.

Diode lasers have an FWHM (Full Width at Half Maximum) in the range of about 6-10 MHz. This means it can sit on top of one absorption line. Different wavelength lasers can be selected to give the slope or shape of the Boltzmann factor. Then the temperature of the exhaust can be calculated. These lasers can be modulated at different frequencies. This allows the different detectors with lock-in amplifiers to be used to differentiate between the lasers illuminating the same spot.

According to the present invention, the detectors are positioned at the focus of the collecting optics.

Different sources need different detector systems. For a broadband light source, one or more filters are positioned in front of the detectors. Array detectors can be used to image strips of the road. This allows one to capture the entire exhaust plume and then to get absolute amounts of the exhaust of a vehicle, irrelevant to the position or height of the tailpipe.

For a diode laser source, the source 610 and the detector 630 are placed on the same optical axis 655, as shown in FIG. 7. The spherical mirror 650 serves as the collecting optics for collecting the scattered light scattered from the surface of the lane and focusing the collected light onto the detector 630. The laser source is brought into the mirror housing with optical fiber. The laser can be outside of the housing.

Figure 8A:
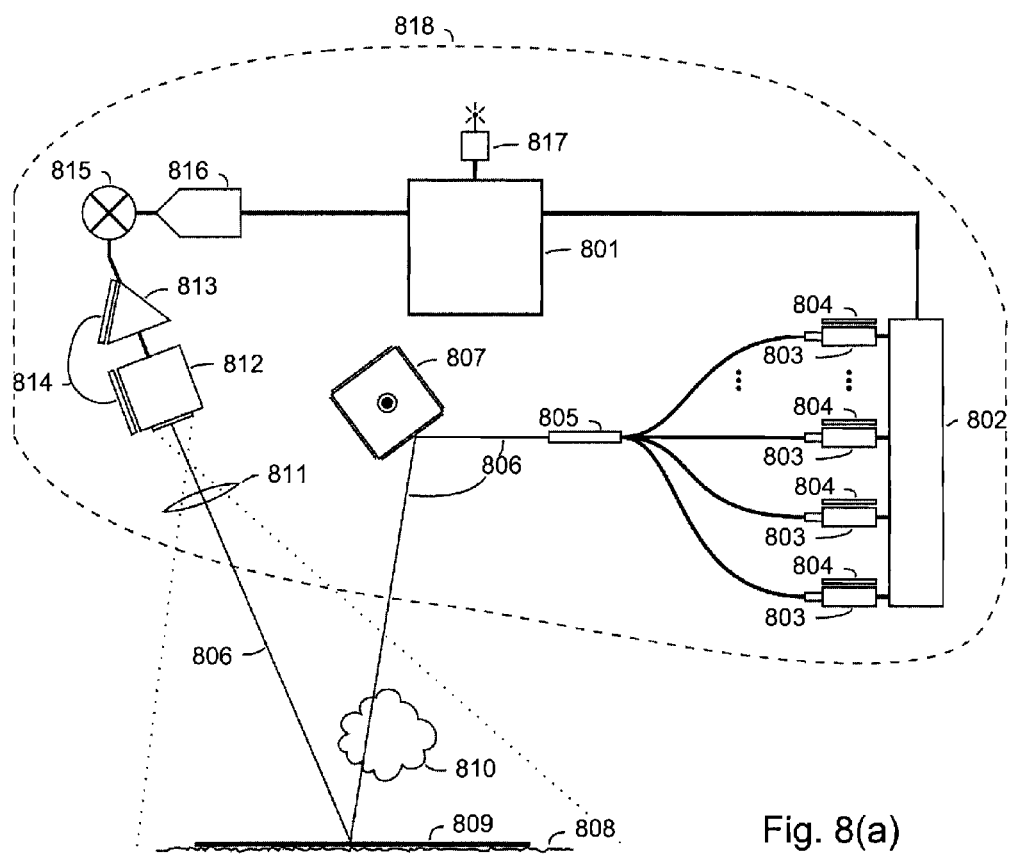
FIG. 8(a) shows schematically a device for scanning a laser across the roadway according to one embodiment of the present invention.
Figure 8B:
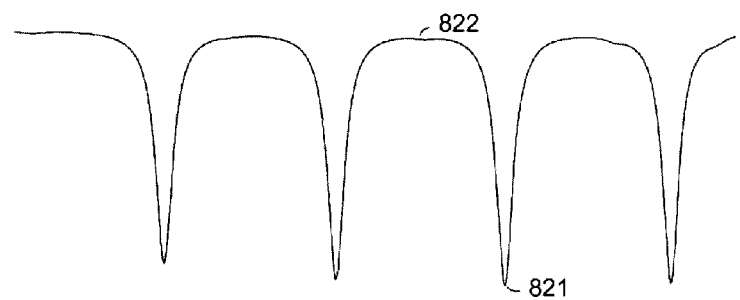
FIG. 8(b) shows two possible wavelengths on a transmission spectrum which may be used for DIAL according to one embodiment of the present invention.
Figure 9A:
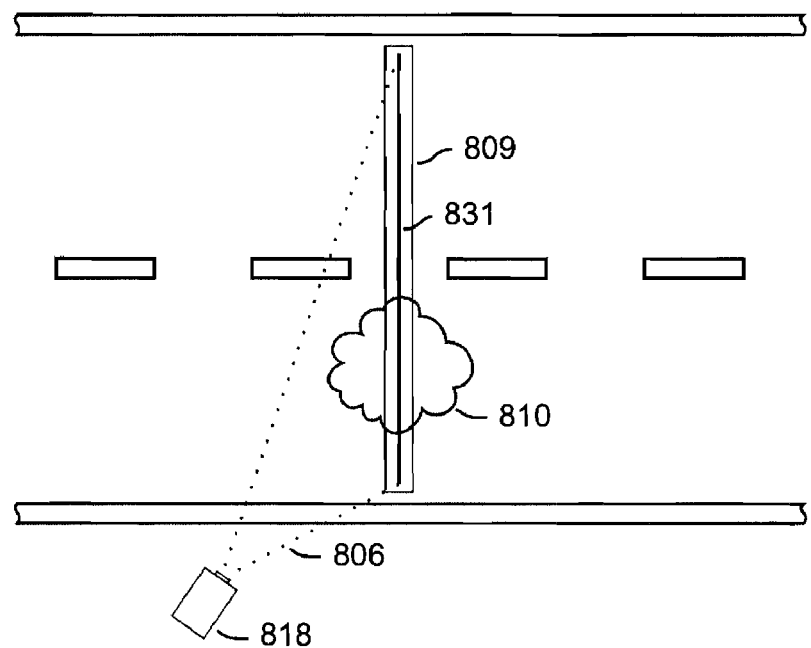
FIG. 9(a) shows schematically a device scanning a single laser line across the road according to one embodiment of the present invention.
Figure 9B:
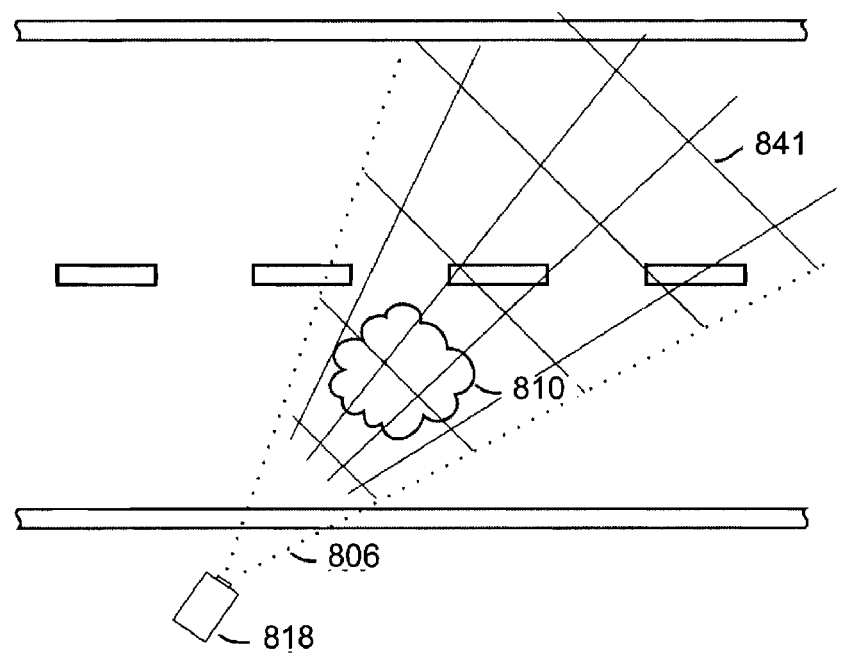
FIG. 9(b) shows schematically a device scanning multiple laser lines across the road according to one embodiment of the present invention.

Referring to FIGS. 8 and 9, one embodiment of the apparatus 818 uses coherent light sources 803 or lasers and a broadband, single-element detector 812. One or more coherent light sources 803 emitting at different selected wavelengths are time-modulated 802 by a controller 801. In the case of tunable diode lasers, the wavelengths can be selected by setting the temperature of each laser 803 with a corresponding cooling device 804. The resulting time-modulated light beams are optically combined 805, and sent through positioning optics 807. The positioned light beam 806 passes through a gaseous plume 810, reflecting off of some substantially reflective material 809. The reflected light beam 806 passes through detection optics 811 and is focused into an opto-electronic detector 812. The electric signal from the detector 812 passes into a low-noise amplifier 813. The detector 812 as well as the amplifier 813 can be placed in a cooling mechanism 814 to increase the sensitivity and stability of the detection. The resulting signal is then passed through a demodulation circuit 815 and into an analog-to-digital converter 816. Ultimately the measurement is digitized and processed by the controller 801. The results can be locally displayed or recorded as well as transmitted to a remote location by some communication mechanism 817.

The controller 801 can be a computing device such as an embedded computer in conjunction with application specific digital electronics such as a Field Programmable Gate Array (FPGA).

Each coherent source 803 emits at a specified wavelength, which is chosen to detect the presence or absence of an absorption peak. When placed on an absorption peak 821, or "on line", a light source 803 can be used to measure the concentration or alternatively absolute amounts of gas in the light path 806. When placed on an absorption trough 822, or "off line" measurements with a coherent source 803 can be used to eliminate the properties of the environment. In other words, it is desirable to know how much light returns to the detector over the path with a lower sensitivity, but at approximately the same wavelength. This is preferably done in the wings of the in between the lines. A differential absorption cross-section is calculated and put in to the DIAL (Differential Absorption LIDAR) equation.

For remote vehicle exhaust measurements, some gases of interest are CO, $CO_2$, $O_2$, NO, various hydrocarbons, etc. Since the absorption peaks 821 for such gases exist over a wide range of wavelengths including visible, ultraviolet and infrared, it is advantageous to pick measurement wavelengths which maximize signal-to-noise while using practical and cost-effective sources 803 and detectors 809.

The coherent sources 803 are typically cooled by a cooling mechanism 804. The cooling mechanism 804 is typically a thermo-electric cooler in conjunction with a temperature measurement device such as a thermistor, which allows the temperature of the source 803 to be precisely controlled electronically with a feedback control system, for example. Adjusting the temperature allows some lasers to be tuned for wavelength. Controlling the temperature has the added benefit of avoiding temperature drift, which can inadvertently modulate the source 803. If the source 803 is substantially stable at a desired wavelength, the cooling mechanism 804 can be omitted simplifying the design as well as lowering its cost.

Since wavelengths of tunable lasers can be swept over many absorption peaks, the controller 801 can pick a peak which maximizes the signal-to-noise ratio. Usually, it will be a wavelength with the largest absorption and the lowest temperature sensitivity for the measured gas while not coinciding with any other present gases. Also, the system can pick a different wavelength in case it detects is some form of interference at the existing wavelength.

The output power of each coherent source 803 can be regulated as well. This can be done with a current feedback system or a photo-diode feedback system or a combination of the two.

The sources can be modulated by direct electrical stimulation 802 or mechanically using an electrically controlled shutter such as a chopper wheel or a liquid crystal shutter. One method of modulating the light source 803 in the time domain is using a constant frequency waveform such as a sine wave or square wave as well as other more complex, orthogonal patterns. Other time-domain modulation techniques, such as shifting the phase between two sources by 90 degrees, are possible as well.

Time-modulating the sources allows the system to ignore background signals or noise by picking a modulation which avoids external light sources. This not only includes any ambient light sources, but also any light emitted by the hot gaseous plume itself. The transmission of light through a plume can be then be consistently measured regardless of the temperature of the plume. Time-modulation also allows the invention to use a single detector 812 by placing each light signal in its own frequency band which can be separated electronically by a demodulation mechanism 815. This reduces the physical complexity of the design as well as replacing high-cost exotic light detection materials with low-cost demodulation electronics or digital computation. Additionally, time-modulation increases the sensitivity of the detector 812 by operating in a band where 1/f noise is lower.

If the sources 803 are not modulated separately in the time domain, other means can be used to detect each source. For example, the system can use multiple detectors, each tuned to a specific optical wavelength, one for each coherent source. One method is to use an optical filter in conjunction with each detector or even use the detector's natural bandwidth to discriminate each light source. Another method involves changing the polarization of each source and using detectors in conjunction with polarization filters.

The function of the optical combiner 805 is to form the separate coherent beams from the sources 803 into a single light beam 806. The optical combiner 805 can be a fused set of fiber optics or a reversed beam splitter, for example. The optical combiner can be eliminated if only one measurement wavelength is desired or if the sources happen to already be in a single beam or if separate positioning optics 807 are used for each source 803.

Typically the positioning optics 807 is a spinning mirror connected to a speed-controlled motor. The rotational speed of the motor determines how fast the light beam is scanned over an area of interest. The scan can be a single line 831 or a series of lines 841 in some pattern which can be used to remotely detect the properties of the gaseous plume of interest. By scanning the light beam 806, the position of the gaseous plume 810 can be determined. Since the speed of the scanning apparatus 807 is controlled, the controlling device 801 can correlate the measurement of the detector 812 with the position of the beam 806.

If the position of the plume is not desired, a line-generating lens 601 can be used, for example, eliminating the need for moving parts. The scanning apparatus 807 can be omitted altogether if a single beam is sufficient for the desired measurement.

The reflector 809 can be made of various materials. Retro-reflective tape or paint can be used, for example. Alternatively, an array of mirrored corner cubes can be attached to the roadway. Other aspects over the choice of material involve whether or not the installation is temporary or permanent. The additional reflector 809 can be omitted if the roadway 808 or other pre-existing background feature is substantially reflective so that a suitable signal-to-noise ratio is achieved with the plume 810 of interest. The reflective surface 809 can be omitted altogether if the source and detector are separated such that the plume 810 is between the two. This requires two separate controllers 801 and possible a phase-lock loop or other means to synchronize the two devices.

Since the reflective surface 809 is on a roadway 808 or some other uncontrolled area given to environmental wear-and-tear, it is reasonable to assume that the reflection will not be uniform over the area of the surface. Because this invention divides the measured region into substantially small beams 806, the reflection over any one beam 806 will be mostly constant. Also, since the measurements can be made relative to a baseline measurement 203, the constant sources of attenuation will divide out of the calculations.

Since this embodiment uses an external reflective surface 809, both the modulated sources 803 as well as the detector 809 can be physically together 818, and controlled by a single controller 801. One advantage of this scheme is that since the modulated sources and the detector can be controlled centrally, the modulated sources can be synchronized with the detector electronics. This eliminates the need for a phase-lock-loop or other synchronizing mechanism in the detector electronics.

The detection section of this embodiment includes focusing optics 811 as well as an electro-optical detector 812 connected to a low-noise amplifier 813. The focusing optics 811 allows the embodiment to image a large area, preferable large enough to see the entire plume of interest 810. The detector 812 can be a semi-conductor photodiode or a thermopile or any such sensitive detection device. The detector is made of a material that can detect light in the desired wavelengths. The low-noise amplifier 813 can consist of any appropriate analog signal processing electronics able to suitably extract the signal of interest from the detector 812.

Conventionally, parallel light sources are utilized to measure gaseous plumes, which is disadvantageous because it requires the measurement system to be as large as the plume itself. This can be impractical if the plume is very large such as one from a smoke stack. This embodiment of the invention uses focused light which allows the entire system 818 to be substantially smaller than the plume 810 itself or the region of interest and fit in a compact and practical space. This potentially makes the device unobtrusive and portable.

The opto-electronic detector 812 as well as the low-noise amplifier 813, can be cooled 814 to increase the sensitivity of the detection. Controlling the temperature has the added benefit of making the detector 812 more stable, eliminating unwanted drift in the measured signal. Various cooling techniques are possible including thermo-electric coolers, a Dewar flask containing some cryogenic liquid, or a Stirling engine. If the existing detector element 812 and the low-noise amplifier 813 are substantially sensitive enough, the cooling mechanism 814 can be omitted altogether saving cost and simplifying the design.

While using only single broadband detector 812 is desirable to keep the system simple, a series of narrow-band or otherwise band-limited detectors can be used if there isn't any one practical detector with contiguous band which contains all of the wavelengths of interest.

Another embodiment replaces the single-element detector 812 with an array of detectors. The detectors are arranged such that the position of each detector element corresponds with a desired measurement location. In this case the arrangement of the detectors will form an image of the plume of interest. Additionally, with the combination of both a positioning optics 807 and an imaging array, 3D measurements can be made of the gaseous plume or the vehicle or any other objects in the field of view using well-known photogrammetry techniques.

Yet another embodiment uses a diffuse, time-modulated broadband source in conjunction with a focal plane array. The array elements can have one or more optical filters masking different areas of the FPA. A FPA can have a motorized filter wheel before, after or in between focusing elements of an imaging lens. Alternatively, the filters can be placed in front of the broadband source. This can improve the signal-to-noise ratio of the gaseous measurement over that of a coherent source by encompassing multiple absorption peaks. Temperature insensitivity can be achieved by encompassing individual absorption bands of a target molecule. The broadband source can be modulated electronically or mechanically to help distinguish it from background radiation. Differently filtered broadband sources can be modulated at different frequencies to differentiate each target gas. Also, the source's position can be modulated so that a single element detector can be used. For example, an optical 1D or 2D spatial-modulator such as a liquid crystal shutter can provide a separate modulation for each desired measurement position.

A further embodiment uses a series of narrow band sources. This embodiment uses light sources which each cover a narrow band of wavelengths. Certain light emitting diodes (LED) can fill this requirement. This method is similar to using a broadband source in conjunction with an optical filter and can similarly improve the signal-to-noise ratio of the gaseous measurement by encompassing multiple absorption peaks. Each light source can be time-modulated as before and detected with a single detector or a detector array. With this approach, filters are not needed for the detector.

While this invention focuses on measuring car exhaust, it can be seen that the invention is not limited to car exhaust, but can measure any form of gaseous phenomenon within some field of view against some reflective background. Alternatively, if the light source and detector element are in line, a reflective background isn't necessary.

Calculating optical mass from light intensity measurements can be generalized by the following equation:

$$I(t) = \int_0^\infty H(v) T(v, t) dv,$$

where, v is the wavelength of light.

t is the time of the measurement.

I(t) is a light intensity measurement at time, t.

$H(v) = I_0(v) H_r(v) H_f(v) H_d(v)$ is the system function.

$I_0(v)$ is the intensity of the light source.

$H_r(v)$ is the attenuation of the reflector.

$H_f(v)$ is the attenuation of the filter.

$H_d(v)$ is the attenuation of the detector.

$$T(v, t) = e^{-\sum_{i=1}^{N} \kappa_i(v) om_i(t)}$$

is the transmittance through the gaseous path, or Beer's law.

$\kappa_i(v)$ is a cross-section for molecule, i.

$om_i(v)$ is the optical-mass for molecule, i.

N is the number of molecules.

It is useful to divide an intensity measurement by a reference measurement at some time, $t_0$ to obtain a relative total transmittance.

$$T_{Total}(t) = \frac{I(t)}{I(t_0)} = \frac{\int_0^\infty H(v) T(v, t) dv}{\int_0^\infty H(v) T(v, t_0) dv}$$

This way, if any part of H(v) is constant over the bandwidth, the constant will cancel out in the division. Usually one of the system terms in H(v) is dominant for each embodiment of the invention. For the embodiment with a broad-band source, $H_f(v)$ is the dominant term and the other terms mostly cancel. For the embodiments of a narrow-band source and a coherent source, $I_0(v)$ is the dominant term, because of its intensity overcomes low reflectance of the road surface. Any of these terms can change over time as a function of environmental conditions. As a result, with a good characterization of the dominant system term, accurate measurements can be made without needing to characterize the other terms.

Also, if the optical mass terms at $t_0$ are zero (such as in a vacuum) then, $T(v, t_0) = 1$, and the equation simplifies to:

$$\frac{I(t)}{I(t_0)} = \frac{\int_0^\infty H(v) T(v, t) dv}{\int_0^\infty H(v) dv}$$

Since all of the terms but $om_i(t)$ are measured or known or cancel, the invention can solve for $om_i(t)$. One way to calculate $om_i(t)$ is to perform a computational numerical solution using a well-known technique like Newton's Method or some similar method. Alternatively, a look-up table can be computed ahead of time for a range of desirable values, or an approximate curve can be fitted to $T_{Total}(om_i)$. If N=1, one such curve is:

$$T_{Total}(om_i) = e^{-a \cdot om_i^b},$$

where a and b are the coefficients.

Once $om_i(t)$ is calculated we can in-turn determine absolute amounts or concentrations.

If more than one cross-section exists in the measured band for the gases present in the path, there is no one-dimensional relationship between transmittance and optical-mass anymore. One way to use such a measurement is to take additional independent measurements in other bands in order to form a system of equations. With a sufficient number of independent measurements the optical-masses can be found. For example, if the invention was configured to measure two bands, one band which contains CO and $CO_2$, and another band which contains only CO, the measurement of the CO band can be removed from the measurement of the $CO/CO_2$ band allowing the invention to in-turn calculate the optical mass of $CO_2$. This method allows the invention to use bands that are cost-effective to measure due to the availability of sources, filters, and detectors, but are heavily populated with cross-sections.

For a coherent source, the integrals are eliminated since we are mostly measuring a single wavelength and the responses H(v) cancel out if they are mostly constant between measurements $t_0$ and t, plus the summation of optical depth is eliminated if there is only one element in the intersection of the set of non-zero cross-sections at that wavelength and the set of optical masses in the path.

$$\frac{I(t)}{I(t_0)} = \frac{e^{-\kappa_i(v_0)om_i(t)}}{e^{-\kappa_i(v_0)om_i(t_0)}} = e^{-\kappa_i(v_0)(om_i(t)-om_i(t_0))}$$

Again, if the optical mass at $t_0$ is zero, the equation simplifies to:

$$\frac{I_{v_0,i}(t)}{I_{v_0,i}(t_0)} = e^{-\kappa_i(v_0)om_i(t)}$$

As an alternative to taking measurements at two different times, the DIAL method can be used where measurements are taken using two coherent sources at different wavelengths, one on-line and the other off-line.

$$\frac{I_{v_1,i}(t)}{I_{v_0,i}(t)} = e^{-(\kappa_i(v_1)-\kappa_i(v_0))om_i(t)}$$

According to the present invention, by taking a picture of an exhaust plume with an infrared or ultraviolet camera, the total mass of a specific gas in that plume is calculated. In the case of vehicle exhaust left behind, one can remotely measure specific gases in the grams per distance. In the case of smoke stack plumes, one can remotely measure specific gases in grams per time the smoke stack is spewing out. All these measurements come directly from the pictures/images. The ability to remotely measure the number of molecules in a plume is made possible by optical mass. It does not matter whether the molecules reside in the path. It is like compressing all the molecules in the path into a 2-D flat surface. It is immaterial that the plume is not uniform in concentration or path length. This technique simply counts the number of molecules in a beam of light.

Figure 10:
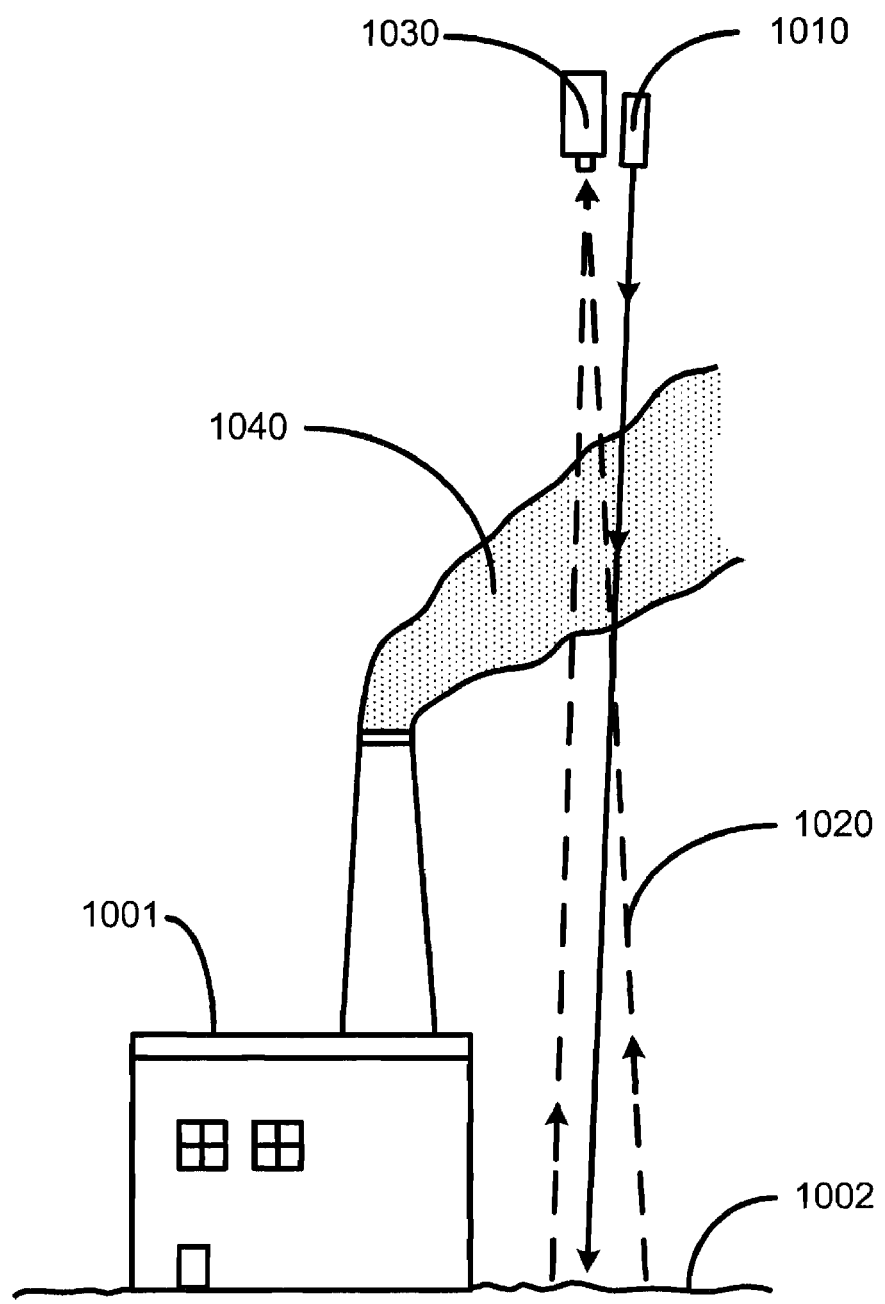
FIG. 10 shows schematically a device for imaging a plume emitted from a factory according to another embodiment of the present invention.
Figure 11:
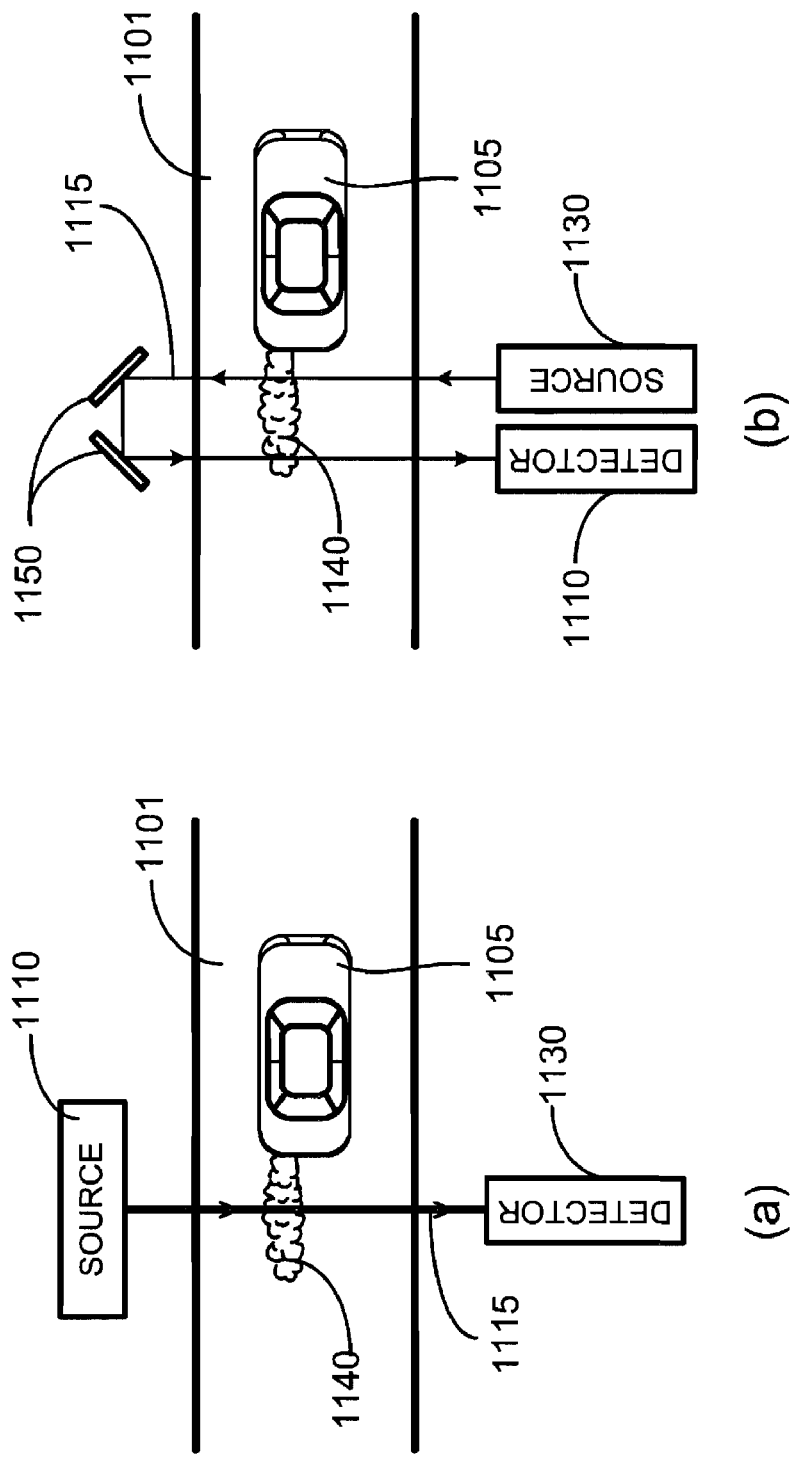
FIG. 11 shows schematically a conventional device for remote sensing of vehicle emission.

In addition to the above applications, the device of the present invention can find applications in a wide spectrum of fields. For example, as shown in FIG. 10, the device can be used to detect and analyze the ingredients and its quantity of exhaust emission/plume 1040 emitted from a factory 1001. The light source 1010 emits a beam of light and transmits the emitted light through an exhaust plume 1040 emitted from the factory to a surface 1002, where the transmitted light 1020 is scattered at the surface 1002. The detector 1030 receives at least one portion of the scattered light 1020 scattered from the surface 1002 and processes the received light therein so as to determine an amount of at least one of components of the exhaust plume 1040. The detector 1030 can be a camera or a photosensor array for taking images of the exhaust plume 1040. Further, the detector 1030 can be on a satellite for taking satellite images of the exhaust plume 1040 for processing.

Other applications include, but not limited to, using the satellite images of atmosphere of the earth to quantify ingredients of the atmosphere so as to identify the source of the global warming. Another application includes quantifying ingredients and amounts of an unknown plume/gas from its images/pictures taken remotely, which may gain a great deal of relevance in anti-terrorism.

In sum, the present invention, among other things, recites a remote sensing device that uses the LIDAR technology. The beam of light emitted from a source is directed downwards, transmitting through the exhaust plume, toward the surface of a traffic lane of a road on which the vehicle is driven. The transmitted light is then scattered at the surface of the traffic lane. A collecting optics is used to collect the scattered light from the surface of the traffic lane. The collected light is delivered to the detector for analyzing the components and providing an amount of the determined component of the exhaust plume. Additionally, according to the present invention, a detector array can be utilized to acquire images of the exhaust plume and the surface of the road, which would enable to unveil the whole picture of gas pollutants in the vehicle exhaust.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A device for quantifying absolute amounts of ingredients of a plume, comprising:
   (a) a light source for emitting a beam of light through the plume to a surface on which the light is scattered;
   (b) a detector for acquiring an image of the plume containing information of absorption of the scattered light scattered from the surface; and
   (c) a processor for processing the acquired image to determine an absolute amount of at least one of ingredients of the plume.

2. The device of claim 1, wherein the processor is configured to perform the functions of:
   (a) choosing a plurality of pixels from the acquired image along a section crossing the plume, each pixel having a pixel area projected on to a surface;
   (b) characterizing an absorption rate of light of each chosen pixel from the acquired image;
   (c) calculating optical mass of each pixel from the characterized absorption rate of the pixel;
   (d) multiplying the optical mass of each pixel and the corresponding adjusted projected pixel area to obtain the number of molecules in each pixel; and
   (e) summing the number of molecules of each pixel to obtain the total number of molecules in the plume.

3. The device of claim 2, wherein the processor is configured to perform further the functions of:
   (f) calculating the number of moles, thereby grams of and ingredients of the plume; and
   (g) calculating the width of the area covered by the pixels to obtain the grams per distance of which the vehicle is leaving behind.

4. The device of claim 2, wherein the optical mass $\mu$ of each pixel is determined by the Beer's Law:

$$\mu = -\ln(I/I_0)/\kappa(v),$$

wherein $(I/I_0)$ is associated with the absorption rate, and $\kappa(v)$ is an absorption cross-section.

5. The device of claim 1, wherein the detector comprises at least one of an infrared camera and an ultraviolet camera with one or more narrow bandpass filters, wherein the one or more narrow bandpass filters incorporate the absorption bands of specific gases.

6. The device of claim 1, wherein the detector comprises a plurality of photosensors, each photosensor generating an electrical signal responsive of the scattered light scattered from the surface, wherein the electrical signal is indicative of the absorption of the received light by the plume.

7. The device of claim 1, wherein the detector comprises a detector array capable of capturing images of the plume.

8. The device of claim 1, wherein the light source comprises a halogen light source and/or glowbar.

9. The device of claim 8, further comprising a collimating/spreading optics for collimating/spreading the emitted light and transmitting the light through the plume to the surface.

10. The device of claim 9, wherein the collimating optics comprises a first concave mirror and a second concave mirror positioned in relation to the source such that the first concave mirror receives the beam of light emitted from the source and reflects the received light to the second concave mirror, the second concave mirror, in turn, collimates the reflected light and transmits the collimated light through the plume to the surface.

11. The device of claim 10, wherein the first concave mirror and the second concave mirror define a focus between, and a chopper is placed on the focus.

12. The device of claim 1, wherein the light source comprises one or more modulated lasers, and/or modulated LEDs.

13. A method for quantifying absolute amounts of ingredients of a plume, comprising the steps of:
   (a) directing a beam of light through the plume to a surface on which the beam of light scattered;
   (b) acquiring an image of the plume containing information of absorption of the scattered light scattered from the surface; and
   (c) processing the acquired image to determine an absolute amount of at least one of ingredients of the plume.

14. The method of claim 13, wherein the processing step comprising the steps of:
   (a) choosing a plurality of pixels from the acquired image along a section crossing the plume, each pixel having a pixel area;
   (b) characterizing an absorption rate of light of each chosen pixel from the acquired image;
   (c) calculating optical mass of each pixel from the characterized absorption rate of the pixel;
   (d) multiplying the optical mass of a pixel and the corresponding pixel area to obtain the number of molecules in the pixel; and
   (e) summing the number of molecules of each pixel to obtain the total number of molecules in the plume.

15. The method of claim 14, wherein the processing step further comprising the steps of:
   (a) calculating the number of moles, thereby grams of and ingredients of the plume; and
   (b) calculating the width of the area covered by the pixels to obtain the grams per distance of which the vehicle is leaving behind.

* * * * *